(12) United States Patent
Prakash et al.

(10) Patent No.: US 7,939,061 B2
(45) Date of Patent: May 10, 2011

(54) CELL AND ENZYME COMPOSITIONS FOR MODULATING BILE ACIDS, CHOLESTEROL AND TRIGLYCERIDES

(75) Inventors: Satya Prakash, Brossard (CA); Mitchell Lawrence Jones, Montreal (CA)

(73) Assignee: Micropharma Limited, Montreal, Quebec (CA)

( * ) Notice: Subject to any disclaimer, the term of this patent is extended or adjusted under 35 U.S.C. 154(b) by 732 days.

(21) Appl. No.: 10/546,990

(22) PCT Filed: Mar. 1, 2004

(86) PCT No.: PCT/CA2004/000306
§ 371 (c)(1),
(2), (4) Date: Jul. 7, 2006

(87) PCT Pub. No.: WO2004/076657
PCT Pub. Date: Sep. 10, 2004

(65) Prior Publication Data
US 2007/0116671 A1 May 24, 2007

Related U.S. Application Data

(60) Provisional application No. 60/450,334, filed on Feb. 28, 2003.

(51) Int. Cl.
*A01N 63/00* (2006.01)
*A01N 63/02* (2006.01)
(52) U.S. Cl. .................. 424/93.4; 424/93.1; 424/93.45
(58) Field of Classification Search .................. None
See application file for complete search history.

(56) References Cited

U.S. PATENT DOCUMENTS

| 4,362,711 A | * | 12/1982 | Cerami | 424/497 |
| 6,217,859 B1 | * | 4/2001 | Chang et al. | 424/93.2 |
| 6,365,148 B1 | * | 4/2002 | Kim et al. | 424/93.1 |

FOREIGN PATENT DOCUMENTS

| CA | 2243352 | 7/1997 |
| EP | 1 433 525 A | 6/2004 |
| JP | 2001069990 A4 | 3/2001 |
| WO | WO 93/05161 A1 | 3/1993 |
| WO | WO 97/16529 A2 | 5/1997 |
| WO | WO 98/27199 A | 6/1998 |
| WO | WO 99/27953 A3 | 6/1999 |
| WO | WO 01/88095 A | 12/2001 |

OTHER PUBLICATIONS

Liu et al. "Alginate-pectin-polylysine particulate as potential controlled release formulation". J. Pharm. Pharmacol. 1999, 51:141-149.*
Corzo et al. Journal of Dairy Science. 1999, vol. 82, No. 3, pp. 466-471.*
Christiaens et al. Applied and Environmental Microbiology. 1992, vol. 58, No. 12, pp. 3792-3798.*
Shah et al. Australian Jouranl of Dairy Technology, 2000, vol. 55, No. 3, pp. 139-144.*
Thornton et al. (Gastroenterology. 1995, vol. 108, No. 4, AGA Abstracts, A928.*
De Smet, I. et al., "In vitro study of bile salt hydrolase (BSH) activity of BSH isogenic *Lactobacillus plantrarum* 80 strains and estimation of cholesterol lowering through enhanced BSH activity", Microbial Ecology in Health and Disease, 1994, pp. 315-329, vol. 7, No. 6.
Chang, T. et al., Artificial cells for bioencapsulation of cells and genetically engineered *E. coli*: For cell therapy, gene therapy, and removal of urea and ammonia, Methods in Molecular Biology; Recombinant Protein Protocols: Detection, 1997, pp. 343-358, 1997 Humana Press Inc., New Jersey, USA.
Chang, T. et al., "Therapeutic uses of microencapsulated genetically engineered cells", Molecular Medicine Today, Elsevier, Cambridge, GB, May 1998, pp. 221-227.
Taranto, M. P. et al., "Effect of *Lactobacillus reuteri* on the prevention of hypercholesterolemia in mice", Journal of Dairy Science, Mar. 2000, pp. 401-403, vol. 83, No. 3, USA.
De Boever, P. et al., "Protective effect of the bile salt hydrolase-active *Lactobacillus reuteri* against bile salt cytotoxicity", Applied Microbiology and Biotechnology, Jun. 2000, pp. 709-714, vol. 53, No. 6.
Casas, I. et al., "Validation of the probiotic concept: *Lactobacillus reuteri* confers broad-spectrum protection against disease in humans and animals", Microbial Ecology in Health and Disease, Nov. 2000, pp. 247-285, vol. 12, No. 4.
Jones, M. et al., "Deconjugation of Bile Acids with Immobilized Genetically Engineered *Lactobacillus plantarum* 80 (pCBH1)", 6th International Congress of the Cell Transplant Society, Mar. 2003, Atlanta, USA (Poster).
Jones, M. et al., "Deconjugation of Bile Acids with Immobilized Genetically Engineered *Lactobacillus plantarum* 80 (pCBH1)", 6th International Congress of the Cell Transplant Society, Mar. 2003, Atlanta, USA (Abstract).
Jones, M., "Microencapsulated Genetically Engineered *Lactobacillus plantarum* 80 (pCBH1) for Bile Acid Deconjugation and its Implication in Lowering Cholesterol", Department of Biomedical Engineering, McGill University, Oct. 2003, Montreal, Canada.
Jones, M. et al., "Microencapsulated Genetically Engineered *Lactobacillus plantarum* 80 (pCBH1) for Bile Acid Deconjugation and its Implication in Lowering Cholesterol", Journal of Biomedicine and Biotechnology, 2004:1 (2004) 61-69.
Jones, M. et al., "Deconjugation of Bile Acids with Immobilized Genetically Engineered *Lactobacillus plantarum* 80 (pCBH1)", Applied Bionics and Biomechanics, 2005, vol. 2, No. 1, pp. 31-38.

(Continued)

*Primary Examiner* — Vera Afremova
(74) *Attorney, Agent, or Firm* — Bereskin & Parr LLP; Noel Courage

(57) ABSTRACT

The invention relates to immobilized or encapsulated enzyme and/or cells to lower bile acids and cholesterol. The invention also relates to methods of quantitatively measuring bile acids. The invention provides a composition for decreasing the amount of a target compound in the gastrointestinal tract of an animal, comprising: a) a biologically active agent which decreases the amount of the target compound; b) a retainer for retaining the biologically active agent by contacting the agent to limit movement of the agent; and c) a carrier.

32 Claims, 15 Drawing Sheets

OTHER PUBLICATIONS

Wang, X. L. and Shao, J.Y., "New Preparation for Oral Administration of Digestive Enzyme. Lactase Complex Microcapsules", Biomaterials, Artificial Cells, and Immobilization Biotechnology, 1993, pp. 637-646, vol. 21, No. 5.

Buisson, P., et al., "Encapsulation of lipases in aerogels", Journal of Non-Crystalline Solids, 2001, pp. 295-302, vol. 285, No. 1-3, North-Holland Publishing Company, Amsterdam, NL.

Kato, K., et al., "Preparation and Catalytic Performance of Lipases Encapsulated in Sol-Gel Materials", Bioscience Biotechnology and Biochemistry, 2002, pp. 221-223, vol. 66, No. 1.

De Smet, I., et al., "Cholesterol lowering in pigs through enhanced bacterial bile salt hydrolase activity", British Journal of Nutrition, 1998, pp. 185-194, vol. 79.

De Boever, P. and Verstraete, W., Bile salt deconjugation by *Lactobacillus plantarum* 80 and its implication for bacterial toxicity, Journal of Applied Microbiology, 1999, pp. 345-352, vol. 87.

Begley, M., et al., "Bile Salt Hydrolase Activity in Probiotics", Applied and Environmental Microbiology, 2006, pp. 1729-1738, vol. 72, No. 3.

Fávaro-Trindade, C.S., et al. "Microencapsulation of *L. acidophilus* (Ia-05) and *B. lactis* (Bb-12) and evaluation of their survival at the pH values of the stomach and in bile", Journal of Microencapsulation, 2002, pp. 485-494, vol. 19, No. 4.

Ye, Z., et al., "Cultivation of *Lactobacillus* in microcapsule", Wei Sheng Wu Xue Bao, Oct. 2000, pp. 507-512, vol. 40, No. 5 (Abstract Only).

Martoni, C., et al., "Investigation of Microencapsulated BSH Active *Lactobacillus* in the Simulated Human GI Tract", Journal of Biomedicine and Biotechnology, 2007, pp. 1-9, vol. 2007.

Garrigues, C. et al., "Characterisation of *Bifidobacterium animalis* subsp. lactis BB-12 and other probiotic bacteria using genomics, transcriptomics and proteomics", The Australian Journal of Dairy Technology, 2005, pp. 84-92, vol. 60, No. 2.

Ahn, Y.T. and Kim, H.U., "Bile salts deconjugtion of lactic acid bacteria found in the feces of normal Korean adults and in fermented milk products", Kor. J. Anim. Sci., 1999, pp. 183-192, vol. 41, No. 2.

Ahn, Y.T., et al., "Study on Bile Salts Deconjugation of Lactic Acid Bacteria Found in the Feces of Normal Korean Adults in Fermented Milk Products", Journal of Korean Livestock, 1999, pp. 183-192, vol. 41, No. 2. (translation).

* cited by examiner

SEQUENCE LISTING

```
<160> NUMBER OF SEQ ID NOS: 10

<210> SEQ ID NO 1
<211> LENGTH: 975
<212> TYPE: DNA
<213> ORGANISM: Lactobacillus plantarum

<400> SEQUENCE: 1
atgtgtactg ccataactta tcaatcttat aataattact tcggtagaaa tttcgattat      60
gaaatttcat acaatgaaat ggttacgatt acgcctagaa aatatccact agtatttcgt     120
aaggtggaga acttagatca ccattatgca ataattggaa ttactgctga tgtagaaagc     180
tatccacttt actacgatgc gatgaatgaa aaaggcttgt gtattgcggg attaaatttt     240
gcaggttatg ctgattataa aaaatatgat gctgataaag ttaatatcac accatttgaa     300
ttaattcctt ggttattggg acaattttca agtgttagag aagtgaaaaa gaacatacaa     360
aaactaaact tggttaatat taattttagt gaacaattac cattatcacc gctacattgg     420
ttggttgctg ataaacagga atcgatagtt attgaaagtg ttaaagaagg actaaaaatt     480
tacgacaatc cagtaggtgt gttaacaaac aatcctaatt ttgactacca attatttaat     540
ttgaacaact atcgtgcctt atcaaatagc acacctcaaa atagttttc ggaaaaagtg      600 gatttagata gttatagtag aggaatgggc ggactaggat tacctggaga cttgtcctca     660
atgtctagat ttgtcagagc cgcttttact aaattaaact cgttgccgat gcagacagag     720
agtggcagtg ttagtcagtt tttccatata ctagggtctg tagaacaaca aaaagggcta     780
tgtgaagtta ctgacggaaa gtacgaatat acaatctatt cttcttgttg tgatatggac     840
aagggagttt attactatag aacttatgac aatagtcaaa ttaacagtgt caatttaaac     900
catgagcact tggatacgac tgaattaatt tcttatccat tacgatcaga agcacaatac     960
tatgcagtta actaa                                                      975

<210> SEQ ID NO 2
<211> LENGTH: 324
<212> TYPE: PRT
<213> ORGANISM: Lactobacillus plantarum

<400> SEQUENCE: 2

Met Cys Thr Ala Ile Thr Tyr Gln Ser Tyr Asn Asn Tyr Phe Gly Arg
1               5                   10                  15

Asn Phe Asp Tyr Glu Ile Ser Tyr Asn Glu Met Val Thr Ile Thr Pro
            20                  25                  30
```

```
Arg Lys Tyr Pro Leu Val Phe Arg Lys Val Glu Asn Leu Asp His His
         35                  40                  45
Tyr Ala Ile Ile Gly Ile Thr Ala Asp Val Glu Ser Tyr Pro Leu Tyr
 50                  55                  60
Tyr Asp Ala Met Asn Glu Lys Gly Leu Cys Ile Ala Gly Leu Asn Phe
 65                  70                  75                  80
Ala Gly Tyr Ala Asp Tyr Lys Lys Tyr Asp Ala Asp Lys Val Asn Ile
                 85                  90                  95
Thr Pro Phe Glu Leu Ile Pro Trp Leu Leu Gly Gln Phe Ser Ser Val
                100                 105                 110
Arg Glu Val Lys Lys Asn Ile Gln Lys Leu Asn Leu Val Asn Ile Asn
                115                 120                 125
Phe Ser Glu Gln Leu Pro Leu Ser Pro Leu His Trp Leu Val Ala Asp
            130                 135                 140
Lys Gln Glu Ser Ile Val Ile Glu Ser Val Lys Glu Gly Leu Lys Ile
145                 150                 155                 160
Tyr Asp Asn Pro Val Gly Val Leu Thr Asn Asn Pro Asn Phe Asp Tyr
                165                 170                 175
Gln Leu Phe Asn Leu Asn Asn Tyr Arg Ala Leu Ser Asn Ser Thr Pro
            180                 185                 190
Gln Asn Ser Phe Ser Glu Lys Val Asp Leu Asp Ser Tyr Ser Arg Gly
        195                 200                 205
Met Gly Gly Leu Gly Leu Pro Gly Asp Leu Ser Ser Met Ser Arg Phe
210                 215                 220
Val Arg Ala Ala Phe Thr Lys Leu Asn Ser Leu Pro Met Gln Thr Glu
225                 230                 235                 240
Ser Gly Ser Val Ser Gln Phe Phe His Ile Leu Gly Ser Val Glu Gln
                245                 250                 255
Gln Lys Gly Leu Cys Glu Val Thr Asp Gly Lys Tyr Glu Tyr Thr Ile
            260                 265                 270
Tyr Ser Ser Cys Cys Asp Met Asp Lys Gly Val Tyr Tyr Tyr Arg Thr
275                 280                 285
Tyr Asp Asn Ser Gln Ile Asn Ser Val Asn Leu Asn His Glu His Leu
        290                 295                 300
Asp Thr Thr Glu Leu Ile Ser Tyr Pro Leu Arg Ser Glu Ala Gln Tyr
305                 310                 315                 320
Tyr Ala Val Asn

<210> SEQ ID NO 3
<211> LENGTH: 2493
<212> TYPE: DNA
<213> ORGANISM: Homo sapiens

<400> SEQUENCE: 3
actgcgactc gagacagcgg cccggcagga cagctccaga atgaaaatgc ggttcttggg     60
gttggtggtc tgtttggttc tctggcccct gcattctgag gggtctggag ggaaactgac    120
agctgtggat cctgaaacaa acatgaatgt gagtgaaatt atctcttact ggggattccc    180
tagtgaggaa tacctagttg agacagaaga tggatatatt ctgtgcctta accgaattcc    240
tcatgggagg aagaaccatt ctgacaaagg tcccaaacca gttgtcttcc tgcaacatgg    300
cttgctggca gattctagta actgggtcac aaaccttgcc aacagcagcc tgggcttcat    360
tcttgctgat gctggttttg acgtgtggat gggcaacagc agaggaaata cctggtctcg    420
gaaacataag acactctcag tttctcagga tgaattctgg gctttcagtt atgatgagat    480
```

```
ggcaaaatat gacctaccag cttccattaa cttcattctg aataaaactg gccaagaaca    540
agtgtattat gtgggtcatt ctcaaggcac cactataggt tttatagcat tttcacagat    600
ccctgagctg gctaaaagga ttaaaatgtt ttttgccctg ggtcctgtgg cttccgtcgc    660
cttctgtact agccctatgg ccaaattagg acgattacca gatcatctca ttaaggactt    720
atttggagac aaagaatttc ttccccagag tgcgttttttg aagtggctgg gtacccacgt    780
ttgcactcat gtcatactga aggagctctg tggaaatctc tgttttcttc tgtgtggatt    840
taatgagaga aatttaaata tgtctagagt ggatgtatat acaacacatt ctcctgctgg    900
aacttctgtg caaaacatgt tacactggag ccaggctgtt aaattccaaa agtttcaagc    960
ctttgactgg ggaagcagtg ccaagaatta ttttcattac aaccagagtt atcctcccac    1020
atacaatgtg aaggacatgc ttgtgccgac tgcagtctgg agcgggggtc acgactggct    1080
tgcagatgtc tacgacgtca atatcttact gactcagatc accaacttgg tgttccatga    1140
gagcattccg gaatgggagc atcttgactt catttggggc ctggatgccc cttggaggct    1200
ttataataaa attattaatc taatgaggaa atatcagtga aagctggact tgagctgtgt    1260
accaccaagt caatgattat gtcatgtgaa atgtgtttg cttcatttct gtaaaacact     1320 tgttttctt tcccaggtct tttgtttttt tatatccaag aaaatgataa ctttgaagat     1380
gcccagttca ctctagtttc aattagaaac atactagcta ttttttcttt aattagggct    1440
ggaataggaa gccagtgtct caaccatagt attgtctctt taagtctttt aaatatcact    1500
gatgtgtaaa aaggtcatta tatccattct gtttttaaaa tttaaaatat attgactttt    1560
tgcccttcat aggacaaagt aatatatgtg ttggaatttt aaaattgtgt tgtcattggt    1620
aaatctgtca ctgacttaag cgaggtataa aagtacgcag ttttcatgtc cttgccttaa    1680
agagctctct agtctaacgg tcttgtagtt agagatctaa atgacatttt atcatgtttt    1740
cctgcagcag gtgcatagtc aaatccagaa atatcacagc tgtgccagta ataaggatgc    1800
taacaattaa ttttatcaaa cctaactgtg acagctgtga tttgacacgt tttaattgct    1860
caggttaaat gaaatagttt tccggcgtct tcaaaaacaa attgcactga taaaacaaaa    1920
acaaaagtat gttttaaatg cttttgaagac tgatacactc aaccatctat attcatgagc    1980
tctcaatttc atggcaggcc atagttctac ttatctgaga agcaaatccc tgtgagact     2040 ataccactat tttttctgag attaatgtac tcttggagcc cgctactgtc gttattgatc    2100
acatctgtgt gaagccaaag ccccgtggtt gcccatgaga agtgtccttg ttcatttca    2160 cccaaatgaa gtgtgaacgt gatgtttcg gatgcaaact cagctcaggg attcattttg    2220
tgtcttagtt ttatatgcat ccttattttt aatacacctg cttcacgtcc ctatgttggg    2280
aagtccatat ttgtctgctt tcttgcagc atcatttcct tacaatactg tccggtggac    2340
aaaatgacaa ttgatatgtt tttctgatat aattacttta gctgcactaa cagtacaatg    2400
cttgttaatg gttaatatag gcagggcgaa tactactttg taacttttaa agtcttaaac    2460
ttttcaataa aattgagtga gacttatagg ccc                                2493
```

<210> SEQ ID NO 4
<211> LENGTH: 399
<212> TYPE: PRT
<213> ORGANISM: Homo sapiens

<400> SEQUENCE: 4

Met Lys Met Arg Phe Leu Gly Leu Val Val Cys Leu Val Leu Trp Pro
1               5                   10                  15

```
Leu His Ser Glu Gly Ser Gly Lys Leu Thr Ala Val Asp Pro Glu
            20                  25                  30

Thr Asn Met Asn Val Ser Glu Ile Ile Ser Tyr Trp Gly Phe Pro Ser
        35                  40                  45

Glu Glu Tyr Leu Val Glu Thr Glu Asp Gly Tyr Ile Leu Cys Leu Asn
50                  55                  60

Arg Ile Pro His Gly Arg Lys Asn His Ser Asp Lys Gly Pro Lys Pro
65                  70                  75                  80

Val Val Phe Leu Gln His Gly Leu Leu Ala Asp Ser Ser Asn Trp Val
                85                  90                  95

Thr Asn Leu Ala Asn Ser Ser Leu Gly Phe Ile Leu Ala Asp Ala Gly
            100                 105                 110

Phe Asp Val Trp Met Gly Asn Ser Arg Gly Asn Thr Trp Ser Arg Lys
        115                 120                 125

His Lys Thr Leu Ser Val Ser Gln Asp Glu Phe Trp Ala Phe Ser Tyr
130                 135                 140

Asp Glu Met Ala Lys Tyr Asp Leu Pro Ala Ser Ile Asn Phe Ile Leu
145                 150                 155                 160

Asn Lys Thr Gly Gln Glu Gln Val Tyr Tyr Val Gly His Ser Gln Gly
                165                 170                 175

Thr Thr Ile Gly Phe Ile Ala Phe Ser Gln Ile Pro Glu Leu Ala Lys
            180                 185                 190

Arg Ile Lys Met Phe Phe Ala Leu Gly Pro Val Ala Ser Val Ala Phe
        195                 200                 205

Cys Thr Ser Pro Met Ala Lys Leu Gly Arg Leu Pro Asp His Leu Ile
210                 215                 220

Lys Asp Leu Phe Gly Asp Lys Glu Phe Leu Pro Gln Ser Ala Phe Leu
225                 230                 235                 240

Lys Trp Leu Gly Thr His Val Cys Thr His Val Ile Leu Lys Glu Leu
                245                 250                 255

Cys Gly Asn Leu Cys Phe Leu Leu Cys Gly Phe Asn Glu Arg Asn Leu
            260                 265                 270

Asn Met Ser Arg Val Asp Val Tyr Thr Thr His Ser Pro Ala Gly Thr
        275                 280                 285

Ser Val Gln Asn Met Leu His Trp Ser Gln Ala Val Lys Phe Gln Lys
290                 295                 300

Phe Gln Ala Phe Asp Trp Gly Ser Ser Ala Lys Asn Tyr Phe His Tyr
305                 310                 315                 320

Asn Gln Ser Tyr Pro Pro Thr Tyr Asn Val Lys Asp Met Leu Val Pro
                325                 330                 335

Thr Ala Val Trp Ser Gly Gly His Asp Trp Leu Ala Ser Val Tyr Asp
            340                 345                 350

Val Asn Ile Leu Leu Thr Gln Ile Thr Asn Leu Val Phe His Glu Ser
        355                 360                 365

Ile Pro Glu Trp Glu His Leu Asp Phe Ile Trp Gly Leu Asp Ala Pro
370                 375                 380

Trp Arg Leu Tyr Asn Lys Ile Ile Asn Leu Met Arg Lys Tyr Gln
385                 390                 395
```

<210> SEQ ID NO 5
<211> LENGTH: 4027
<212> TYPE: DNA
<213> ORGANISM: Lactobacillus acidophilus

<400> SEQUENCE: 5

```
ttttcttaag tctatcttaa aaaaaagata ggcttttat tatgcctatt aaataacatt     60
ataagctgtt attttgatt tactcgattc agtgagccac aatataggtg gctatagtca    120
aagctcgcgc acttaataat atataactta tcaagctaat agtattttgt cagaaagaag   180
agagatacga tgtcaaacga tagacaaaag gtggtcagta aaggctacaa atactttatg   240
gtatttctct gcacgttaac tcaagctgtt ccatatggaa tcgctcaatt aattcaacct   300
ttatttgttc accctctagt taatactttt cattttacat tagcttctta cacattaatt   360
tttacttttg gggctgtcgt agggtcttta gtttcaccat tagttggtaa ggctttacaa   420
aaagtaaact ttaaaatttt atatctgatt ggtatttgtc tttcagctgg agcatatgta   480
atttttggaa ttagcacaaa gttacctggc ttttatttag ctggaattat ttgtatggtt   540
ggttcaacct tttattctgg tcaaggtgtt ccatggatta tcaaccactg gtttccgttt   600
aaaggacgcg gcgttgcttt aggtttagca ttctgcggtg gctcgattgg tgatattttc   660
ctccaaccta ttcccagga aattttaaag catttcatga ccggtaatac taaaactggt   720
cacttaactt ccatggcacc tttctttatc tttgctattg ctttgctaat agttggattg   780
attattgcgg cttttattag agtaccaaag aaagatgaaa tcttagcttc tgctcaagaa   840
gttgagcaaa accggcatga agctgctcaa aagcaagcac atgaatttca aggctggagc   900
ggtaaacaag ttctacatat gaaatggttc tggattttta gtattggatt tttaattatc   960
ggcttaggct tggcctcgtt aaacgaagac tatgcggcct tccttgatac taaattatcc  1020
ttaactgaag tcggaatgat tggctcgta tttggactcg ctggtatcat cggaaatatt  1080
tctggaggtt attatttga taagttcggc acagccaaat caatggcata tgcaggaata  1140
atgttaatta tagctatcct aatgatgatc tttattagcc ttcatcctta tggcgatcgc  1200
attaatttct acgctggtat gggttgggcc tttacaagtg gtctatctgt ctttagctat  1260
atgtctggtc ccgcattat gtcaaaaagc ttatttggtg caaaagccca aggtgttaac  1320
ttaggttaca ttagcctggc atatgctgtt ggttttgcaa ttggcgcccc attatttggc  1380
gtcataaaag gcgctaccag ttttacaact gcttggtgct gcactacttt ctttgtagca  1440
attggtttta tattattaat ttttgcagct attaaaatta gcaaatgca aaaaaatatt  1500
gtcgtcagca aaccaaatat tattttagat aagtaattag tttagaaaga aggtaattac  1560
atgtctactg atgtcgctac taaagataag gtcgttagca aaggctataa atattttatg  1620
gttttccttt gtatattaac ccaagccatt ccttacggga ttgctcaaaa tattcaacct  1680
ttgtttatcc accctttagt taatactttt cactttacct agcatcata tacattaatc  1740
tttacgtttg gggcagtttt tgcttcagtt gcttcgccat ttattggtaa agcattagag  1800
aaagttaatt tcagacttat gtatttaatc ggtattggtc tttccgctat tgcctatgta  1860
atctttggaa ttagtacaaa actaccagga ttctatattg ccgctatcat ttgtatgatt  1920
ggctcaactt tttattccgg tcaaggtgtg ccttgggtta ttaaccactg gttccctgca  1980
aaaggacgtg gagctgctct aggaattgcc ttctgcggtg gctcaattgg taatattttc  2040
ttacaacctg caacgcaagc tattttaaag cactttatga ctggtaatac taagaccggt  2100
cacttgactt caatggcacc attttcatc ttcgcagttg ctctattagt aattggtata  2160
gttattgcct gctttattag aactcctaag aaagatgaaa tcgttatttc tgatgctgag  2220
ttagctgaaa gcaagaaaga agcagaattg gctaaagcta aggaatttaa aggctggact  2280
agtaaacaag tttacaaat gaatggttc tggattttca gtcttggttt tctaattatt  2340
ggcttaggct tagcttcctt aaatgaagat tatgcagcct tccttgatac taaactttca  2400
```

-continued

```
ctaacaaatg ttggtctcat tggatcaatg tacggtgttg gttgtttaat tggaaatgtt    2460
tccggtggat tcttatttga taaatttggt actgctaaat caatgaccta tgctgtctgc    2520
atgtatgttt tatccatctt aatgatggtt ctgatcagtt ttcaacctta tggcgctcac    2580
gtaagtaaaa ttgcaggtat tgcttacgct atcttctgtg tttagccgt atttagctac     2640 atgtctggtc ccgcatttat ggctaaggac ctctttggtt caagagatca gggtgtaatg    2700
ttaggatacg ttggtttggc ttatgcgatt ggatatgcta ttggtgctcc attattcgga    2760
attattaaag gaaaagccag ctttacagtc gcttggtact tcatgattgc ctttgtagca    2820
attggtttta tcatcttagt atttactgtt attcaaatta agagaagtca aaagaaatac    2880
atcattcagc aagaaactaa aactactgct gaataattaa ggaggatttt aaaatgtgta    2940
ctggtttaag atttactgat gatcaaggaa atctatactt tggacgtaac ttagacgttg    3000
gacaagatta tggtgaaggt gtaattatta cacctcgcaa ctatcctctt ccatataaat    3060
ttttagataa tacaactact aaaaaggctg ttatcggcat gggaattgta gtcgatggct    3120
atccttctta ctttgactgt ttcaatgaag atggtttggg aattgctggt ctaaacttcc    3180
cgcattttgc caaattcagt gacggtccaa ttgatgaaaa attaattta gcttcttacg     3240 aaattatgct ctgggtcacc caaaacttta ctaaagtcag cgacgtaaaa gaagctttaa    3300
aaaacgttaa cttagttaat gaggctatta attcatcgtt tgcagttgct cctcttcact    3360
ggattattag tgacaaagat gaagctatta ttgtcgagat ttcaaagcaa tacggtatga    3420
aagtctttga tgataggctt ggcgttctaa ctaacagccc agattttaat tggcaccta    3480 ctaatctcgg caactatact ggcttagatc cacatgacgc tacagctcaa agctggaacg    3540
gtcaaaaagt tgctccatgg ggcgttggca ctggcagctt aggtttacca ggtgatagca    3600
ttccagcaga tcgctttgtt aaagcagctt acttaaatgt taattatcca actgttaaag    3660
gtaaaaaagc taacgttgcc aagttcttta acatcttaaa gtctgttgcg atgattaaag    3720
gcagcgtagt taacaaacaa ggtagcaatg aatacactgt ctatactgct tgctattctg    3780
ctgctactaa gacttattac tgcaactttg aaaatgattt tgaattaaag acttacaagt    3840
tagacgatga aacaatgaac gccgataagc taattactta ttaaattaat ttctacaaaa    3900
atactaataa aaaaattcag agcttaaaaa ctctgaattt tttgtttaat catcttttc    3960 tgatttaata actttcttag aaatagcatc aatttctact tcatgtttac ttgaacctga    4020
ttcaaca                                                              4027
```

<210> SEQ ID NO 6
<211> LENGTH: 316
<212> TYPE: PRT
<213> ORGANISM: Lactobacillus acidophilus

<400> SEQUENCE: 6

Met Cys Thr Gly Leu Arg Phe Thr Asp Asp Gln Gly Asn Leu Tyr Phe
1               5                   10                  15

Gly Arg Asn Leu Asp Val Gly Gln Asp Tyr Gly Glu Gly Val Ile Ile
            20                  25                  30

Thr Pro Arg Asn Tyr Pro Leu Pro Tyr Lys Phe Leu Asp Asn Thr Thr
        35                  40                  45

Thr Lys Lys Ala Val Ile Gly Met Gly Ile Val Val Asp Gly Tyr Pro
    50                  55                  60

Ser Tyr Phe Asp Cys Phe Asn Glu Asp Gly Leu Gly Ile Ala Gly Leu
65                  70                  75                  80

Asn Phe Pro His Phe Ala Lys Phe Ser Asp Gly Pro Ile Asp Gly Lys

```
                    85                  90                  95
Ile Asn Leu Ala Ser Tyr Glu Ile Met Leu Trp Val Thr Gln Asn Phe
                100                 105                 110

Thr Lys Val Ser Asp Val Lys Glu Ala Leu Lys Asn Val Asn Leu Val
            115                 120                 125

Asn Glu Ala Ile Asn Ser Ser Phe Ala Val Ala Pro Leu His Trp Ile
        130                 135                 140

Ile Ser Asp Lys Asp Glu Ala Ile Ile Val Glu Ile Ser Lys Gln Tyr
145                 150                 155                 160

Gly Met Lys Val Phe Asp Asp Arg Leu Gly Val Leu Thr Asn Ser Pro
                165                 170                 175

Asp Phe Asn Trp His Leu Thr Asn Leu Gly Asn Tyr Thr Gly Leu Asp
            180                 185                 190

Pro His Asp Ala Thr Ala Gln Ser Trp Asn Gly Gln Lys Val Ala Pro
        195                 200                 205

Trp Gly Val Gly Thr Gly Ser Leu Gly Leu Pro Gly Asp Ser Ile Pro
    210                 215                 220

Ala Asp Arg Phe Val Lys Ala Ala Tyr Leu Asn Val Asn Tyr Pro Thr
225                 230                 235                 240

Val Lys Gly Lys Lys Ala Asn Val Ala Lys Phe Phe Asn Ile Leu Lys
                245                 250                 255

Ser Val Ala Met Ile Lys Gly Ser Val Val Asn Lys Gln Gly Ser Asn
            260                 265                 270

Glu Tyr Thr Val Tyr Thr Ala Cys Tyr Ser Ala Ala Thr Lys Thr Tyr
        275                 280                 285

Tyr Cys Asn Phe Glu Asn Asp Phe Glu Leu Lys Thr Tyr Lys Leu Asp
    290                 295                 300

Asp Glu Thr Met Asn Ala Asp Lys Leu Ile Thr Tyr
305                 310                 315

<210> SEQ ID NO 7
<211> LENGTH: 1087
<212> TYPE: DNA
<213> ORGANISM: Clostridium perfringens

<400> SEQUENCE: 7
gagtataatg taaatttgaa atatagtat tatttactta tataaaatct aatgaggagt      60
gagtgtttat gtgtacagga ttagccttag aaacaaaaga tggattacat ttgtttggaa    120
gaaatatgga tattgaatat tcatttaatc aatctattat atttattcct aggaatttta    180
aatgtgtaaa caaatcaaac aaaaaagaat taacaacaaa atatgctgtt cttggaatgg    240
gaactatttt tgatgattat cctaccttttg cagatggtat gaatgaaaag ggattagggt    300
gtgctggctt aaatttccct gtttatgtta gctattctaa agaagatata gaaggtaaaa    360
ctaatattcc agtatataat ttcttattat gggttttagc taattttagc tcagtagaag    420
aggtaaagga agcattaaaa aatgctaata tagtggatat acctattagc gaaaatattc    480
ctaatacaac tcttcattgg atgataagcg ataatacagg aaagtctatt gtggttgaac    540
aaacaaagga aaaattaaat gtatttgata ataatattgg agtattaact aattcaccta    600
cttttgattg gcatgtagca aatttaaatc aatatgtagg tttgagatat aatcaagttc    660
cagaatttaa gttaggagat caatctttaa ctgctttagg tcaaggaact ggtttagtag    720
gattaccagg ggactttaca cctgcatcta gatttataag agtagcattt ttaagagatg    780
caatgataaa aaatgataaa gattcaatag acttaattga attttttccat atattaaata    840
```

```
atgttgctat ggtaagagga tcaactagaa ctgtagaaga aaaaagtgat cttactcaat      900
atacaagttg catgtgttta gaaaaggaa tttattatta taatacctat gaaaataatc       960
aaattaatgc aatagacatg aataaagaaa acttagatgg aaatgaaatt aaaacatata     1020 aatcaacaa aactttaagt attaatcatg taaattagtt tgttgcatgg gcgtgtatca      1080
aaacttt                                                                1087
```

<210> SEQ ID NO 8
<211> LENGTH: 329
<212> TYPE: PRT
<213> ORGANISM: Clostridium perfringens

<400> SEQUENCE: 8

```
Met Cys Thr Gly Leu Ala Leu Glu Thr Lys Asp Gly Leu His Leu Phe
1               5                   10                  15

Gly Arg Asn Met Asp Ile Glu Tyr Ser Phe Asn Gln Ser Ile Ile Phe
            20                  25                  30

Ile Pro Arg Asn Phe Lys Cys Val Asn Lys Ser Asn Lys Glu Leu
        35                  40                  45

Thr Thr Lys Tyr Ala Val Leu Gly Met Gly Thr Ile Phe Asp Asp Tyr
 50                  55                  60

Pro Thr Phe Ala Asp Gly Met Asn Glu Lys Gly Leu Gly Cys Ala Gly
65                  70                  75                  80

Leu Asn Phe Pro Val Tyr Val Ser Tyr Ser Lys Glu Asp Ile Glu Gly
                85                  90                  95

Lys Thr Asn Ile Pro Val Tyr Asn Phe Leu Leu Trp Val Leu Ala Asn
            100                 105                 110

Phe Ser Ser Val Glu Glu Val Lys Glu Ala Leu Lys Asn Ala Asn Ile
        115                 120                 125

Val Asp Ile Pro Ile Ser Glu Asn Ile Pro Asn Thr Thr Leu His Trp
130                 135                 140

Met Ile Ser Asp Ile Thr Gly Lys Ser Ile Val Val Glu Gln Thr Lys
145                 150                 155                 160

Glu Lys Leu Asn Val Phe Asp Asn Asn Ile Gly Val Leu Thr Asn Ser
                165                 170                 175

Pro Thr Phe Asp Trp His Val Ala Asn Leu Asn Gln Tyr Val Gly Leu
            180                 185                 190

Arg Tyr Asn Gln Val Pro Glu Phe Lys Leu Gly Asp Gln Ser Leu Thr
        195                 200                 205

Ala Leu Gly Gln Gly Thr Gly Leu Val Gly Leu Pro Gly Asp Phe Thr
210                 215                 220

Pro Ala Ser Arg Phe Ile Arg Val Ala Phe Leu Arg Asp Ala Met Ile
225                 230                 235                 240

Lys Asn Asp Lys Asp Ser Ile Asp Leu Ile Glu Phe Phe His Ile Leu
                245                 250                 255

Asn Asn Val Ala Met Val Arg Gly Ser Thr Arg Thr Val Glu Glu Lys
            260                 265                 270

Ser Asp Leu Thr Gln Tyr Thr Ser Cys Met Cys Leu Glu Lys Gly Ile
        275                 280                 285

Tyr Tyr Tyr Asn Thr Tyr Glu Asn Asn Gln Ile Asn Ala Ile Asp Met
290                 295                 300

Asn Lys Glu Asn Leu Asp Gly Asn Glu Ile Lys Thr Tyr Lys Tyr Asn
305                 310                 315                 320

Lys Thr Leu Ser Ile Asn His Val Asn
                325
```

<210> SEQ ID NO 9
<211> LENGTH: 1685
<212> TYPE: DNA
<213> ORGANISM: Bifidobacterium bifidum

<400> SEQUENCE: 9

```
gcggcatgta ctacgaggag ggcatgcact ataccgccgc atcggaacgg cagaagcggg      60
tcgactgttt cagagccgcc gagatccttt accggcacgc ggccggccgc ggcaatgcga     120
tcggatggct gtgcctgggg tacgtgtacg cgtacgaccg ctgcaagggt agatacttcc     180
gctcgtatta caacaatttc ggcgaagttc gccaaaaacc ggatacggac gttttggcat     240
acgagtgctt tcgtcatgcg gccgaagcgg ggatcgcgga gggctgctac aagctgggag     300
acgtgctggc cgagggcaga ggctgtgcgg ctgatcatgc gaaggcgctc gacatgttcc     360
tgcgggagta catgtgtgac ggatattgcg gcaggcacat tttacacgaa atacatgatt     420
gaggaggacg atactatgga tgaggtagtc aaagcagatt cttccgcggg caaaacttaa     480
gattttccca gcaagtgacg cttaccatga acacgcaagc aagaaaatca cggcaaatca     540
tggaaaggag tccatatgtg cactggtgtc cgtttctccg acgatgaggg aaacatgtat     600
ttcggccgta atctcgactg gagcttctcc tacggcgaga ccattctggt cactccgcga     660
ggctaccagt acgactatga gtatggggcc gaaggtaaaa gcgaaccgaa tgcggtgatc     720
ggcgtgggcg tggtcatgac cgaccgcccc atgtatttcg actgcgccaa cgagcatggc     780
ctggccattg ccggactgaa cttccctggg tacgcctcct tgcacacga gccggtcgaa     840
ggaaccgaaa acgtcgctac cttcgaattc ccgctgtggg tggcgcgcaa tttcgacagt     900
gtcgacgaag tcgaagaggc gttgaagaac gtgacgctcg tttcgcaggt cgtgcccggc     960
cagcaggaat ccctgctgca ctggttcatt ggtgacggca cccgcagcat cgtcgtcgag    1020
cagatggctg acggcatgca cgttcatcat gacgatgtgg acgtgcttac caaccagccg    1080
accttcgact tcatatggaa aaacctgcgc aactacatgt gtgtgagcaa cgagatggcg    1140
gagccgacca cttggggcaa ggcggaactg agcgcatggg gtgccggtgt gagcatgcac    1200
ggcattcccg gtgacgtgag ttcgccgtcg cgtttcgtac gcgtcgccta caccaacacg    1260
cactatccgc agcagaacaa cgaagctgct aatgtgtctc gtctgttcca cacgctggtt    1320
tccgtgcaaa tggttgacgg catgtccaag atgggcaacg gccagttcga gcgcacgctg    1380
ttcaccagtg gctattccgg gaaaaccaac acgtattaca tgaacacgta tgaggatccg    1440
gcgatccgct cgtttgccat gtccgacttc gacatggatt cgagcgagct gatcaccgcc    1500
gattgattcc gggaatttcg agttcgaaga ttccagttcc gaagattccg cagtgatcgc    1560
actatatgga cagcataaaa gggcacaacg tcgcaacctg aaccgcaccc cgattgttgg    1620
actgaagaaa ttcagattcg atgatcggag gtgcggttca ggttgcgacg ttgtgccttg    1680
aattt                                                               1685
```

<210> SEQ ID NO 10
<211> LENGTH: 316
<212> TYPE: PRT
<213> ORGANISM: Bifidobacterium bifidum

<400> SEQUENCE: 10

```
Met Cys Thr Gly Val Arg Phe Ser Asp Asp Glu Gly Asn Met Tyr Phe
1               5                   10                  15
Gly Arg Asn Leu Asp Trp Ser Phe Ser Tyr Gly Glu Thr Ile Leu Val
            20                  25                  30
```

```
Thr Pro Arg Gly Tyr Gln Tyr Asp Tyr Glu Tyr Gly Ala Glu Gly Lys
        35                  40                  45

Ser Glu Pro Asn Ala Val Ile Gly Val Gly Val Val Met Thr Asp Arg
    50                  55                  60

Pro Met Tyr Phe Asp Cys Ala Asn Glu His Gly Leu Ala Ile Ala Gly
65              70                  75                  80

Leu Asn Phe Pro Gly Tyr Ala Ser Phe Ala His Glu Pro Val Glu Gly
                85                  90                  95

Thr Glu Asn Val Ala Thr Phe Glu Phe Pro Leu Trp Val Ala Arg Asn
            100                 105                 110

Phe Asp Ser Val Asp Glu Val Glu Glu Ala Leu Lys Asn Val Thr Leu
        115                 120                 125

Val Ser Gln Val Val Pro Gly Gln Gln Glu Ser Leu Leu His Trp Phe
        130                 135                 140

Ile Gly Asp Gly Thr Arg Ser Ile Val Val Glu Gln Met Ala Asp Gly
145                 150                 155                 160

Met His Val His His Asp Asp Val Asp Val Leu Thr Asn Gln Pro Thr
                165                 170                 175

Phe Asp Phe His Met Glu Asn Leu Arg Asn Tyr Met Cys Val Ser Asn
            180                 185                 190

Glu Met Ala Glu Pro Thr Thr Trp Gly Lys Ala Glu Leu Ser Ala Trp
        195                 200                 205

Gly Ala Gly Val Ser Met His Gly Ile Pro Gly Asp Val Ser Ser Pro
        210                 215                 220

Ser Arg Phe Val Arg Val Ala Tyr Thr Asn Thr His Tyr Pro Gln Gln
225                 230                 235                 240

Asn Asn Glu Ala Ala Asn Val Ser Arg Leu Phe His Thr Leu Val Ser
                245                 250                 255

Val Gln Met Val Asp Gly Met Ser Lys Met Gly Asn Gly Gln Phe Glu
            260                 265                 270

Arg Thr Leu Phe Thr Ser Gly Tyr Ser Gly Lys Thr Asn Thr Tyr Tyr
        275                 280                 285

Met Asn Thr Tyr Glu Asp Pro Ala Ile Arg Ser Phe Ala Met Ser Asp
        290                 295                 300

Phe Asp Met Asp Ser Ser Glu Leu Ile Thr Ala Asp
305                 310                 315
```

CELL AND ENZYME COMPOSITIONS FOR MODULATING BILE ACIDS, CHOLESTEROL AND TRIGLYCERIDES

FIELD OF THE INVENTION

The invention relates to immobilized or encapsulated enzyme and/or cells to modulate bile acids, cholesterol and triglyceride levels in a subject. The invention also relates to methods of quantitatively measuring bile acids and triglycerides.

BACKGROUND OF THE INVENTION

Bile acids are important physiological agents that are required for the disposal of cholesterol and the absorption of dietary lipids and lipid soluble vitamins. Bile salts are the water-soluble end products of cholesterol, and are synthesized de novo in the liver. During normal enterohepatic circulation (EHC), the average bile salt pool is secreted into the duodenum twice during each meal, or an average of 6-8 times per day for the purpose of forming mixed micelles with the products of lipid digestion. During intestinal transit, most of the secreted bile salt is absorbed in the terminal ileum and is returned to the liver via the portal vein. The bile salt pool is replenished by hepatic synthesis of new bile from serum cholesterol. It has been shown that upon surgical, pharmacological or pathological interruption of the EHC, bile salt synthesis is increased up to 15-fold, leading to an increased demand for cholesterol in the liver. Therefore, various studies have been reported suggesting possible oral bacterial preparations for reducing serum cholesterol. Though effective, these methods still have several limitations. For example, a normal daily intake of 250 ml of yogurt would only correspond to 500 milligram of cell dry weight (CDW) of bacteria, and of those bacteria ingested only 1% would survive gastric transit limiting the overall therapeutic effect. There are also some practical concerns regarding the production, cost, and storage of such a product (De Smet et al., 1998). Further, oral administration of live bacterial cells can pose problems. For example, when given orally, large amounts of live bacterial cells can stimulate host immune response, they can be retained in the intestine, and repeated large doses could result in their replacing the normal intestinal flora (De Boever and Verstraete, 1999; Christiaens et al., 1992). In addition, risk of systemic infections, deleterious metabolic activities, adjuvant side-effects, immuno-modulation and risk of gene transfer has limited their use (De Boever and Verstraete, 1999; Christiaens et al., 1992). Metabolic activities and immuno-modulation, have limited its clinical use (De Boever et al., 2000).

Although bile acids are important to normal human physiology, bile acids can be cytotoxic agents when produced in pathologically high concentrations. As well, when ileal transport of bile acids is defective due to a congenital defect, resection of the ileum, or disease, elevated intraluminal concentrations of bile acids can induce the secretion of electrolytes and water causing diarrhea and dehydration. Therefore, various studies suggested methods for removing bile acids by either directly preventing the reabsorption of bile acids or by removing bile acids using chemical binders such as bile acid sequestrants (BAS). These methods have several limitations. For example, common BAS Cholestyramine resin (Locholest, Questran), Colesevelam (Welchol), and Colestipol (Colestid) are well documented to exhibit major adverse effects such as nausea, bloating, constipation, and flatulence (Christiaens et al., 1992).

Current treatments for elevated blood cholesterol include dietary management, regular exercise, and drug therapy with fibrates, bile acid sequestrants, and statins. Such therapies are often sub-optimal and carry a risk for serious side effects. Dietary intervention, whereby lipid intake is restricted is generally the first line of treatment (Lichtenstein, 1998; Ornish and Denke, 1994; Ornish et al., 1998). Studies show that complete elimination of dietary cholesterol and limiting fat content to less than ten percent of the daily caloric intake can effect a mere four percent regression of atherosclerotic plaques after five years when combined with stress management and aerobic exercise (Dunn-Emke et al., 2001). However, the combined restricted vegetarian diet (free of meat, fish, chicken, vegetable oils and all dairy fat products) and aerobic approach, is unrealistic for all but the most dedicated individuals. A variety of dietary supplements or specific foods e.g. brans, psylliums, guar gum, lecithins, whey, red wines, fish oils and ginseng root extract have been reported to reduce high blood cholesterol or its consequences. The mechanisms are varied and include cholesterol sequestering, chelating, entrapment and oxidation inhibition. Such regimens generally lower the blood cholesterol level by ten percent or less. In addition, none of these dietary interventions have been shown to arrest or cure atherosclerosis or other high blood cholesterol associated diseases.

Pharmacologic agents such as fibric acid derivatives (fibrates), nicotinic acid, bile acid sequestrants (BAS), estrogen replacement therapy, and hydroxymethyl glutaryl-coenzyme A (HMG-CoA) reductase inhibitors (statins) are also available for the treatment of high cholesterol. From among the agents listed above, the statins are considered to have the most potential for treatment. Currently lovastatin, pravastatin, zocor, fluvastatin and atorvastatin are being used for clinical lowering of cholesterol. Although effective at reducing cholesterol levels, they are nevertheless expensive (Attanasio et al., 2001; Hodgson and Cohen, 1999; Prosser et al. 2000; Reckless, 1996). Some are known to have side effects and are associated. Naturally occurring bacteria can significantly lower serum cholesterol levels by hydrolyzing bile salts in the intestinal tract but only 1% of free bacteria ingested survive the GI transit. However, live bacterial cells can cause a host immune response and can be retained in the intestine replacing the natural intestinal flora (Taranto et al., 2000; Anderson and Gilliland, 1999; Chin et al., 2000). It has been shown that certain strains of bacteria act directly on bile acids in the gastrointestinal tract and may be beneficial in reducing serum cholesterol levels in this way (Taranto et al., 2000; Anderson and Gilliland, 1999; De Smet et al. 1994). Control of cholesterol through oral live bacterial cell therapy, is based on the demonstration that naturally occurring bacteria such as *Lactobacillus acidophilus, Lactobacillus bulgaricus*, and *Lactobacillus reuteri* can significantly lower serum cholesterol levels (Taranto et al., 2000; Anderson and Gilliland, 1999; De Smet et al. 1994). For example, *Lactobacillus reuteri* was used to decrease the serum cholesterol in pigs through interaction of free bacteria with the host's bile salt metabolism (De Smet et al., 1998). The underlying mechanism for the reduction of serum cholesterol appears to be the capacity of *Lactobacillus* to hydrolyze bile salts in the intestinal tract (Anderson and Gilliland, 1999; De Smet et al. 1994). Elevated Bile Salt Hydrolase (BSH) activity leads to an increase in the loss of bile acids from the ECH and to a greater demand for cholesterol by the liver (De Smet et al. 1994) (FIG. 8). In the work of De Smet et al., the BSH activity of BSH overproducing. *Lactobacillus plantarum* 80 (pCBHl) was shown to have a considerable cholesterol lowering capacity (De Smet et al. 1994). The bile salt hydrolase enzyme, contained on the multicopy plasmid (pCBH1), carries out the deconjugation of bile salts through catalysis of hydrolysis of the amide bond that conjugates bile acids to glycine or taurine (Christiaens et al., 1992; De Smet et al. 1994) (FIG. 9).

While work in this field has been very promising, several limiting factors to the oral administration of free bacteria have been identified. The therapeutic potential of free bacteria is hampered by inherent limitations in their use. For example, of those free bacteria ingested only 1% survive gastric transit limiting the overall therapeutic effect (De Smet et al. 1994). Also, oral administration of live bacterial cells can cause a host immune response, and can be detrimentally retained in the intestine replacing the natural intestinal flora (Taranto et al., 2000; Chin et al., 2000; De Boever and Verstraete, 1999). Furthermore, there are some practical concerns regarding the production, cost, and storage of products containing free bacteria (De Boever and Verstraete, 1999). Thus, concerns of safety and practicality have prevented the regular use of this promising therapy in clinical practice.

Other problematic diseases or disorders arise from disrupted lipid metabolism. For example, steathorrea results from damage to the pancreas or bowel (eg. inflammation resulting from pancreatitis). The pancreas is the gland that produces digestive enzymes to metabolize carbohydrates and lipids. The resulting condition, known as exocrine or pancreatic insufficiency, leads to weight loss and very foul-smelling stools or diarrhea. Chronic pancreatitis can lead to diabetes and pancreatic calcification, a condition where small, hard deposits form in the pancreas. There is a need for new treatments that allow patients to fully digest food.

Encapsulation and immobilization patents include U.S. Pat. No. 6,565,777, U.S. Pat. No. 6,346,262, U.S. Pat. No. 6,258,870, U.S. Pat. No. 6,264,941, U.S. Pat. No. 6,217,859, U.S. Pat. No. 5,766,907 and U.S. Pat. No. 5,175,093. Artificial cell microencapsulation is a technique used to encapsulate biologically active materials in specialized ultra thin semi-permeable polymer membranes (Chang and Prakash, 1997; Chang, 1964). The polymer membrane protects encapsulated materials from harsh external environments, while at the same time allowing for the metabolism of selected solutes capable of passing into and out of the microcapsule. In this manner, the enclosed material is retained inside and separated from the external environment, making microencapsulation particularly useful for biomedical and clinical applications (Lim and Sun, 1980; Sefton et al, 2000; Chang, 1999). Studies show that artificial cell microcapsules can be used for oral administration of live genetically engineered cells that can be useful for therapeutic functions (Prakash and Chang, 2000; Prakash and Chang, 1996). Examples of applications of microencapsulation of enzymes, cells and genetically engineered microorganisms are xanthine oxidase for Lesch-Nyhan disease; phenylalanine ammonia lyase for pheny, ketonuria and E. coli DH5 cells for lowering urea, ammonia and other metabolites (Chang and Prakash 2001). Although the live cells remain immobilized inside the microcapsules, microencapsulation does not appear to hinder their growth kinetics (Prakash and Chang, 1999). The microcapsules remain intact during passage through the intestinal tract and are excreted intact with the stool in about 24 hours. The cells are retained inside, and excreted with, the intact microcapsules addressing many of the major safety concerns associated with the use of live bacterial cells for various clinical applications. The membranes of the microcapsules are permeable to smaller molecules, and thus the cells inside the microcapsules metabolize small molecules found within the gut during passage through the intestine (Chang and Prakash, 1997; Prakash and Chang, 2000; Prakash and Chang, 1996; Prakash and Chang, 1999; Prakash and Chang, 1996a, Prakash and Chang, 1999a).

SUMMARY OF THE INVENTION

The invention relates to compositions and methods that are useful for modulating levels of a target compound, such as bile or triglycerides, in an animal. Typically, the compositions and methods modulate levels in the gastrointestinal system of the animal. Adjusting the levels in the gastrointestinal system affects levels in serum and other fluids, tissues and excrement. The compositions and methods are useful for reducing bile and cholesterol levels in an animal to prevent or treat a disease or disorder characterized by increased bile and cholesterol levels (or a disease or disorder having increased bile or cholesterol as a risk factor, such as heart disease or cancer). The compositions and methods are also useful for providing trigylceride-hydrolysis products, such as fatty acids and glycerol, to an animal in need thereof, for example, an animal having pancreatitis or other disruptions of the pancreas or bowel.

The compositions are optionally orally administered or implanted in the animal. The compositions act on target compound produced by the animal or consumed by the animal, for example target compound in food or nutritional supplements. The compositions are optionally pharmaceutical compositions, food compositions and/or nutraceutical compositions. The compositions optionally comprise:

i) a biologically active agent which modulates target compound levels in an animal, for example, by degrading target compound in an animal to reduce target compound levels. The agent is optionally an enzyme for modulating lipid or bile metabolism, such as BSH, for deconjugating bile acids to form target-degradation compounds. This has the effect of reducing bile acid levels. The agent is also optionally a lipase, which breaks down lipids, such as triglycerides and their esters, to form target-degradation compounds such as fatty acids. The agent also optionally comprises a cell, such as a bacterial cell, expressing the enzyme;

ii) a retainer for retaining the biologically active agent, for example by immobilizing it on a surface and/or encapsulating it. This has the effect of isolating the agent and reducing its movement. The retainer optionally comprises a capsule, such as a capsule comprising a semi-permeable membrane, and/or a support, such as a polymer structure. The retainer is optionally a retainer means for retaining the agent; and iii) a carrier. The carrier is optionally a pharmaceutically acceptable carrier, such as saline solution.

In one embodiment, the compositions further comprise a collector for collecting a target-degradation compound formed as a result of the agent's reaction with the target compound. Collection permits the target-degradation compound to be either excreted by the animal or absorbed by the animal's gastrointestinal system.

The invention also includes methods comprising contacting a biologically active agent (for example, a composition of the invention) with a target compound in an animal to, for example, degrade target compound in an animal to reduce target compound levels. The methods optionally modulate lipid or bile metabolism, with an agent such as BSH, for deconjugating bile acids to form target-degradation compounds. This has the effect of reducing bile acid levels. The methods optionally use a lipase, which breaks down lipids, such as triglycerides and their esters, to form target-degradation compounds such as fatty acids. The methods optionally use a cell, such as a bacterial cell, expressing the enzyme. The methods optionally involve oral administration or implantation in the animal. In the methods, the biologically active agent is optionally retained in a retainer, for example immobilized on a surface and/or encapsulated. This has the effect of isolating the agent and reducing its movement in the methods. The methods optionally further comprise collecting a target-degradation compound formed as a result of the agent's reaction with the target compound. In one embodiment, a bile acid is deconjugated and then, its by-product, DCA, is captured, for example by precipitation and collection in a capsule, where it is held until it is excreted.

In one embodiment of the invention, the present inventors have shown that immobilized or encapsulated genetically engineered cells, such as Lactobacillus plantarum 80 cells expressing BSH, are a biologically active agent that efficiently hydrolyzes bile acids and that are useful in the deconjugation of human bile acids.

Another embodiment of the invention relates to cells, for example, immobilized or encapsulated genetically engineered cells, such as Lactobacillus cells expressing lipase, as a biologically active agent that efficiently hydrolyzes lipids and that are useful in the hydrolysis of human lipids.

Accordingly, in an embodiment, the present invention provides a composition of immobilized or encapsulated cells, such as bacteria, and/or enzyme for lowering bile acids and/or cholesterol.

In another embodiment, the present invention provides a composition comprising of at least one immobilized and biologically active agent in an amount sufficient to degrade bile acids or lipids and a carrier. The biologically active agent is optionally any cell expressing or capable of expressing a bile acid degrading enzyme or lipid-degrading enzyme, anaerobic bacteria expressing or capable of expressing a bile acid degrading enzyme or a lipid-degrading enzyme, a bile acid degrading enzyme-containing cell extract, a lipid-degrading enzyme-containing cell extract, a bile acid degrading enzyme itself or a lipid-degrading enzyme itself. Cells or bacteria are optionally genetically engineered. The bacteria is optionally Lactobacillus such as, Lactobacillus plantarum, Lactobacillus reuteri or a combination thereof. Bile acid degrading enzymes include BSH. BSH is optionally lactobacillus plantarum BSH. Lipid degrading enzymes include lipase, such as mammalian or bacterial lipase.

The immobilized biologically active agent is usefully encapsulated or microencapsulated.

In one embodiment, the carrier is intended for oral administration and is optionally in the form of a nutraceutical or functional food product.

The invention includes the use compositions of the invention for use in medicine (eg. as a pharmaceutical substance). The invention also includes the use of compositions of the invention for the manufacture of a medicament effective against diseases and disorders recited in this application. Unwanted intraluminal bile acids in the gastrointestinal system are associated with bowel diseases. Accordingly, the present invention provides a method for lowering of intraluminal bile acid of patients suffering from a bowel disease, which comprises of administering a bile acid lowering amount of a composition of the present invention.

Naturally occurring bacteria can significantly lower serum cholesterol levels by hydrolyzing bile salts in the intestinal tract. Accordingly, the present invention provides a method for lowering of serum cholesterol of patients, which comprises administering a bile acid lowering amount of a composition of the present invention.

The composition for lowering of intraluminal bile acids or serum cholesterol may be administered singly or in combination with other cholesterol lowering therapeutics.

In another embodiment, the present invention provides a method for lowering of serum cholesterol and/or total body cholesterol of animals for the purpose of producing animal products of reduced cholesterol content, which comprises administering a bile acid lowering amount of a composition of the present invention.

Colon cancer has been linked to diet and the proposed mechanism is that a high fat diet leads to an increased secretion of primary bile salts into the small intestine where the indigenous microflora deconjugates the primary bile acids. Accordingly, the present invention provides a method for preventive therapy of colon cancer in a patient, which comprises administering a bile acid lowering amount of a composition of the present invention.

Urinary levels of sulfated bile acids are known to be significantly elevated in liver disease and hepatobiliary disease. Accordingly, the present invention provides an in vitro diagnostic tool for liver and hepatobiliary diseases and disorders in an animal (eg. a patient), which comprises
  a) support;
  b) a biologically active agent immobilized onto said support;
wherein the immobilized agent allows detection and measurement of bile acid degradation when contacted with a biological sample. The biologically active agent is optionally any cell expressing or capable of expressing a bile acid degrading enzyme, anaerobic bacteria expressing or capable of expressing a bile acid degrading enzyme, a bile acid degrading enzyme-containing cell extract or a bile acid degrading enzyme. Bile acid degrading enzymes include BSH. BSH is optionally lactobacillus plantarum BSH. The diagnostic tool is readily adapted to measure lipids and diagnose a disease or disorder characterized by improper/inadequate lipid hydrolysis in an animal.

The present invention also provides a method for quantitatively measuring bile acids. In an embodiment, the present invention provides an in vitro method for measuring bile acid which comprises
  (a) contacting a biological sample with the tool of the present invention
  (b) contacting a control sample with the tool of the present invention
  (c) comparing the amount of degradation of bile acid in (a) and (b)
wherein a higher level of degradation product compared to control level is indicative of a liver or hepatobiliary disease. The diagnostic tool is readily adapted to quantitatively measure lipids in an animal.

The present invention provides a composition for decreasing the amount of a target compound in the gastrointestinal tract of an animal, comprising:
  i) a biologically active agent which decreases the amount of the target compound;
  ii) a retainer for retaining the biologically active agent by contacting the agent to limit movement of the agent;
  iii) a carrier.

In one embodiment, the retainer limits agent movement by a retainer surface immobilizing the agent and/or by the retainer encapsulating the agent. In a further embodiment, the retainer encapsulates the agent and reduces exposure of the biologically active agent to antibodies and permits exposure of the biologically active agent to nutrients. The retainer optionally comprises a semi-permeable membrane. The semi-permeable membrane also optionally comprises a MWCO of about 3000 D to 950,000 D In one embodiment, the retainer comprises a polymer bead and the agent is immobilized on the bead.

The target compound optionally comprises bile acid or triglyceride and the amount of the target compound is decreased by degrading the target compound to at least one target-degradation compound. In one embodiment, the target compound comprises bile acid and the target-degradation compound comprises DCA. In another embodiment, the target compound comprises triglyceride and the target-degradation compound comprises fatty acid.

The invention further provides for a composition comprising a collector for collecting the target-degradation compound and permitting the animal to excrete or absorb the target-degradation compound from the gastrointestinal tract of the animal. In one embodiment, the retainer comprises the collector. Optionally, the target-degradation compound for collection comprises a DCA precipitate or a fatty acid.

In another embodiment, the biologically active agent is selected from the group consisting of a cell expressing a bile acid degrading enzyme, anaerobic bacteria expressing a bile acid degrading enzyme, a bile acid degrading enzyme-containing cell extract, or a bile degrading enzyme.

In a further embodiment, the biologically active agent is selected from the group consisting of a cell expressing a triglyceride degrading enzyme, anaerobic bacteria expressing a triglyceride degrading enzyme, a triglyceride degrading enzyme-containing cell extract, or a triglyceride degrading enzyme.

The cells optionally comprise a human cell, a fungal cell or a bacterial cell. In a further embodiment the bacteria or cell is genetically engineered. The bacteria optionally comprises at least one of *Lactobacillus plantarum, Lactobacillus reuteri, Bifidobacterium bifidum, Lactobacillus acidophilus*, and *Clostridium perfringens*. Alternatively, the bacteria comprises a combination of *Lactobacillus plantarum*, and *Lactobacillus reuteri*. In one embodiment, the *Lactobacillus plantarum* comprises *Lactobacillus plantarum* 80.

In a further embodiment, the bile acid degrading enzyme comprises BSH. BSH optionally has a nucleotide sequence as shown in one of SEQ. ID. NO. 1, 5, 7 or 9 and an amino acid sequence as shown in one of SEQ. ID. NO. 2, 6, 8 or 10.

In another embodiment, the triglyceride bile acid degrading enzyme comprises lipase. The lipase optionally has a nucleotide sequence as shown in SEQ. ID. NO. 3 and an amino acid sequence as shown in SEQ. ID. NO. 4.

In one embodiment, the biologically active agent is encapsulated or microencapsulated in a membrane made of alginate-polylysine-alginate (APA). Alternatively, the biologically active agent is encapsulated or microencapsulated in a membrane made of Alginate/Poly-l-lysine/Pectin/Poly-l-lysine/Alginate (APPPA), Alginate/Poly-l-lysine/Pectin/Poly-l-lysine/Pectin (APPPP), and Alginate/Poly-L-lysine/Chitosan/Poly-l-lysine/Alginate (APCPA) membranes In another embodiment, the carrier comprises an orally administrable carrier. In a further embodiment, the carrier comprises a nutraceutical or functional food product. Alternatively, the carrier comprises an implantable device.

In one embodiment, the composition comprises a pharmaceutical composition and the carrier comprises a pharmaceutically acceptable carrier.

The invention also provides a method for lowering of intraluminal bile acid of animals suffering from defective ileal transport of bile acids due to a congenital defect, resection of the ileum or a bowel disease or disorder, which comprises administering to the animal a bile acid lowering amount of a composition of the invention.

The invention further provides a method for lowering of intraluminal bile acid or patients, comprising administering to the animal a capsule or immobilized agent comprising:
(a) a first bacteria that deconjugates bile salts and
(b) a second bacteria that precipitates and binds the deconjugated bile salts.

In one embodiment, the first bacteria is *L. plantarum* and the second bacteria is *L. reuteri*.

The invention also provides for a method for lowering serum cholesterol of an animal, comprising administering to the animal a bile acid lowering amount of a composition of the invention.

The invention provides for a method for lowering serum cholesterol and/or total body cholesterol of animals for the purpose of producing animal products of reduced cholesterol content, comprising administering to the animal a bile acid lowering amount of a composition of the invention. In a further embodiment, the composition is administered in combination with another cholesterol lowering therapeutic. The another cholesterol lowering therapeutic is optionally selected from the group consisting of BAS Cholestyramine resin, Colesevelam, Colestipol, statin, probiotic formulation containing other live bacterial cells and neutraceuticals, and natural cholesterol lowering products. In one embodiment, the statin is selected from the group consisting of lovastatin, pravastatin, zocor, fluvastatin, and atorvastatin The invention further provides for a method for preventing or treating colon cancer in an animal, which comprises administering to the animal a bile acid lowering amount of a composition of the invention.

In an embodiment, the invention provides an in vitro diagnostic tool for detecting liver or hepatobiliary disease in a patient, which comprises
a) a support;
b) a biologically active agent immobilized onto the support;
wherein the immobilized agent allows detection and/or measurement of bile acid degradation when contacted with a biological sample.

In one embodiment, the biological sample comprises urine, blood, feces or vomit. The detection is optionally based on a colour indicator wherein a change in colour of the indicator in contact with the biological sample compared to the colour of a control is indicative of bile acid degradation and reduced or increased bile acid in an animal compared to normal animal bile acid degradation is indicative of liver or hepatobiliary disease. The biologically active agent is optionally selected from the group consisting of a cell expressing a bile acid degrading enzyme, anaerobic bacteria expressing a bile acid degrading enzyme, a bile acid degrading enzyme-containing cell extract, or a bile degrading enzyme. The cell is optionally a human cell, a fungal cell or a bacterial cell. The bacteria or cell is also optionally genetically engineered. In one embodiment, the bacteria comprises at least one of *Lactobacillus plantarum, Lactobacillus reuteri, Bifidobaterium bifidum, Lactobacillus acidophilus*, and *Clostridium perfringenes*. Alternatively, the bacteria comprises a combination of *Lactobacillus plantarum*, and *Lactobacillus reuteri*. The *Lactobacillus plantarum* optionally comprises *Lactobacillus plantarum* 80 (pCBH1).

In another embodiment, the bile acid degrading enzyme of the in vitro diagnostic tool comprises BSH. The BSH optionally has a nucleotide sequence as shown in SEQ. ID. NO. 1, 5, 7, or 9 and an amino acid sequence as shown in SEQ. ID. NO. 2, 6, 8, or 10.

In a further embodiment, the immobilized biologically active agent of the in vitro diagnostic tool is encapsulated or microencapsulated. The biologically active agent is optionally encapsulated or microencapsulated in a membrane comprising alginate-polylysine-alginate (APA). Alternatively, the biologically active agent is encapsulated or microencapsulated in a membrane comprising Alginate/Poly-l-lysine/Pectin/Poly-l-lysine/Alginate (APPPA), Alginate/Poly-l-lysine/Pectin/Poly-l-lysine/Pectin (APPPP), and Alginate/Poly-L-lysine/Chitosan/Poly-l-lysine/Alginate (APCPA) membranes The invention also provides for an in vitro method for measuring bile acid comprising
   a) contacting a biological sample with a tool of the invention
   b) contacting a control sample with a tool of the invention
   c) comparing the amount of degradation of bile acid in (a) and (b)
wherein a higher level of degraded bile acid product in (a) than (b) is indicative of a liver or hepatobiliary disease.

The invention provides a method for lowering triglycerides, which comprises administering a triglyceride lowering amount of a composition of the invention.

The invention also provides a method for lowering total body fat of animals for the purpose of producing animal products of reduced fat content, comprising administering a triglyceride lowering amount of a composition of the invention.

The invention further provides a method for preventing or treating steathorrea in a patient, which comprises administering a triglyceride lowering amount of a composition of the invention.

In one embodiment, the invention provides an in vitro diagnostic tool for detecting steathorrea in an animal, which comprises
   a) a support;
   b) a biologically active agent immobilized onto the support;
wherein the immobilized agent allows detection and/or measurement of triglyceride degradation when contacted with a biological sample.

In one embodiment, the biological sample comprises urine, blood, feces or vomit. The detection is optionally based on a colour indicator wherein a change in colour of the indicator in contact with the biological sample compared to the colour of a control is indicative of triglyceride degradation in the animal compared to normal animal triglyceride degradation is indicative of steathorrea. The biologically active agent is optionally selected from the group consisting of a cell expressing a triglyceride degrading enzyme, anaerobic bacteria expressing a triglyceride degrading enzyme, a triglyceride degrading enzyme-containing cell extract, or a triglyceride degrading enzyme. The cell is optionally a human cell, a fungal cell or a bacterial cell. The bacteria or cell is also optionally genetically engineered. In one embodiment, the bacteria comprises at least one of *Lactobacillus plantarum*, *Lactobacillus reuteri*, *Bifidobaterium bifidum*, *Lactobacillus acidophilus*, and *Clostridium perfringenes*. Alternatively, the bacteria comprises a combination of *Lactobacillus plantarum*, and *Lactobacillus reuteri*. The *Lactobacillus plantarum* optionally comprises *Lactobacillus plantarum* 80 (pCBH1).

In another embodiment, the triglyceride degrading enzyme of the in vitro diagnostic tool comprises lipase. The lipase optionally has a nucleotide sequence as shown in SEQ. ID. NO. 3 and an amino acid sequence as shown in SEQ. ID. NO. 4.

In a further embodiment, the immobilized biologically active agent of the in vitro diagnostic tool is encapsulated or microencapsulated. The biologically active agent is optionally encapsulated or microencapsulated in a membrane comprising alginate-polylysine-alginate (APA). Alternatively, the biologically active agent is encapsulated or microencapsulated in a membrane comprising Alginate/Poly-l-lysine/Pectin/Poly-l-lysine/Alginate (APPPA), Alginate/Poly-l-lysine/Pectin/Poly-l-lysine/Pectin (APPPP), and Alginate/Poly-L-lysine/Chitosan/Poly-l-lysine/Alginate (APCPA) membranes.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

Embodiments of the invention are described in relation to the drawings in which.

DETAILED DESCRIPTION OF THE INVENTION

Figure 1:
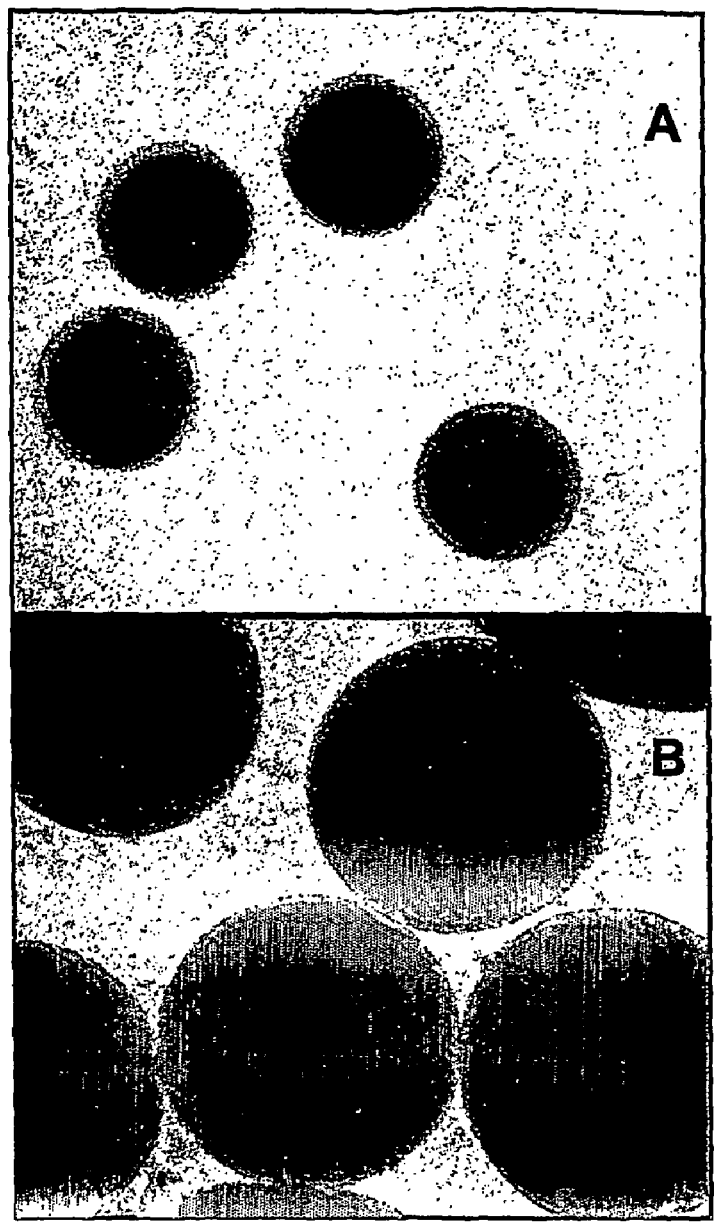
FIG. 1 illustrates a photomicrograph of alginate beads containing immobilized *Lactobacillus plantarum* 80 (pCBH1) cells at 43.75× magnification (A) and at 175× magnifications (B)

The invention relates to compositions and methods that are useful for modulating levels of a target compound, such as bile or triglycerides, in an animal. Typically, the compositions and methods modulate levels in the gastrointestinal system of the animal. Adjusting the levels in the gastrointestinal system affects levels in serum and other fluids, tissues and excrement. The compositions and methods are useful for reducing bile and cholesterol levels in an animal to prevent or treat a disease or disorder characterized by increased bile and cholesterol levels or a disease or disorder having increased bile or cholesterol as a risk factor, such as heart disease or cancer. The compositions and methods are also useful for providing trigylceride-hydrolysis products, such as fatty acids and glycerol, to an animal in need thereof, for example, an animal having pancreatitis or other disruptions of the pancreas or bowel.

The compositions act on target compound produced by the animal or consumed by the animal, for example target compound in food or nutritional supplements. The compositions optionally comprise:

i) a biologically active agent which modulates target compound levels in an animal, for example, by degrading target compound in an animal to reduce target compound levels. The agent is optionally an enzyme for modulating lipid or bile metabolism, such as BSH, for deconjugating bile acids to form target-degradation compounds. This has the effect of reducing bile acid levels. The agent is also optionally a lipase, which breaks down lipids, such as triglycerides and their esters, to form target-degradation compounds such as fatty acids. The agent also optionally comprises a cell, such as a bacterial cell, expressing the enzyme;

ii) a retainer for retaining the biologically active agent, for example by immobilizing it on a surface and/or encapsulating it. This has the effect of isolating the agent and reducing its movement. The retainer optionally comprises a capsule, such as a capsule comprising a semi-permeable membrane, and/or a support, such as a polymer structure. The retainer is optionally a retainer means for retaining the agent; and iii) a carrier.

In one embodiment, the compositions further comprise a collector for collecting a target-degradation compound formed as a result of the agent's reaction with the target compound. Collection permits the target-degradation compound to be either excreted by the animal or absorbed by the animal's gastrointestinal system. The collector optionally contains (holds), binds, metabolizes or precipitates the target-degradation compound. The collector makes the target-degradation compound less bioavailable. The collector is optionally a capsule or polymer surface. The collector is also optionally a chemical associated with the capsule or polymer surface, for example, forming part of a capsule membrane or surface. The chemical may also be located in a space defined by the membrane or polymer surface. Alternatively, the target-degradation compound is physically contained (held) in a space defined by the membrane or polymer surface. The collector is optionally a collection means for collecting the target-degradation compound. In one embodiment, the retainer itself performs the collector function by collecting a target-degradation compound.

The invention also includes methods comprising contacting a biologically active agent (for example, a composition of the invention) with a target compound in an animal to, for example, degrade target compound in an animal to reduce target compound levels. The methods optionally modulate lipid or bile metabolism, with an agent such as BSH, for deconjugating bile acids to form target-degradation compounds. This has the effect of reducing bile acid levels. The methods optionally further comprise collecting a target-degradation compound formed as a result of the agent's reaction with the target compound. In one embodiment, a bile acid is deconjugated and then, its by-product, DCA, is captured, for example by precipitation and collection in a capsule, where it is held until it is excreted.

The invention is described in additional detail below.

The present inventors have demonstrated that immobilized or encapsulated cells or enzymes efficiently hydrolyze bile acids and are useful in the deconjugation of bile acids in animals, such as humans. Immobilized or encapsulated cells or enzymes also efficiently hydrolyze lipids in animals, such as humans. An example of a suitable cell is genetically engineered *Lactobacillus plantarum* 80 (pCBHl) expressing BSH. Results show that immobilized LP80 (pCBHl) is able to effectively break down the conjugated bile acids glycodeoxycholic acid (GDCA) and taurodeoxycholic acid (TDCA) with bile salt hydrolase (BSH) activities of 0.17 and 0.07 µmol DCA/mg CDW/h respectively. In addition, the immobilized or encapsulated cells collect the DCA so that it is excreted. This is a very useful aspect because DCA is toxic and causes diseases, such as cancer. Immobilized live engineered cells are a good agent for the deconjugation of bile acids and provide an effective therapy to lower pathologically high levels of bile acids for prophylaxis or treatment of diseases and disorders caused by high levels of bile acids and/or cholesterol. Immobilized, live engineered cells are also a good agent for the hydrolysis of lipids and provide an effective therapy where the subject is unable to hydrolyze adequate amounts of lipids.

Accordingly, in an embodiment, the present invention provides a composition of immobilized or encapsulated cells, such as bacteria, or enzyme for lowering bile acids and/or cholesterol. The phrase "bile acid lowering amount" as used herein means an amount effective, at dosages and for periods of time necessary to achieve the desired results (e.g. degradation of bile acids and/or lowering of cholesterol). Effective amounts may vary according to factors such as the disease state, age, sex, weight of the animal. Dosage regima may be adjusted to provide the optimum therapeutic response. For example, several divided doses may be administered daily or the dose may be proportionately reduced as indicated by the exigencies of the therapeutic situation.

In another embodiment, the present invention provides a composition of immobilized or encapsulated cells, such as bacteria, or enzyme for lowering triglycerides. The phrase "triglyceride lowering amount" as used herein means an amount effective, at dosages and for periods of time necessary to achieve the desired results (e.g. degradation of triglyceride). Effective amounts may vary according to factors such as the disease state, age, sex, weight of the animal. Dosage regima may be adjusted to provide the optimum therapeutic response. For example, several divided doses may be administered daily or the dose may be proportionately reduced as indicated by the exigencies of the therapeutic situation.

In another embodiment, the present invention provides a composition comprising an immobilized and biologically active agent in an amount sufficient to degrade bile acids in association with a carrier. The composition is optionally a pharmaceutical composition and the carrier is optionally a pharmaceutically acceptable carrier. The biologically active agent may be any cell expressing a bile acid degrading enzyme, anaerobic bacteria expressing a bile acid degrading enzyme, a bile acid degrading enzyme-containing cell extract or a bile acid degrading enzyme. Useful expressing cells include cells "capable of expressing" which means that the cell has an inducible element such that the enzyme is expressed when induced. "Bile acid degrading" means the ability to break down the conjugated bile acids glycodeoxycholic acid (GDCA) and taurodeoxycholic acid (TDCA).

Cells or bacteria may be genetically engineered or produced by other methods, such as irradiation-induced mutation or selection of naturally mutated cells that degrade increased amounts of bile acid compared to a wild type cell. The cells are optionally any cell, such as an animal cell (eg. human cell) or a fungal cell or a bacterial cell as long as they are capable of expressing the enzyme. The bacteria is optionally *Lactobacillus* such as, *Lactobacillus plantarum, Lactobacillus reuteri* or a combination thereof. The bacteria is optionally *Bifidobacterium bifidum, Lactobacillus acidophilus*, or *clostridium perfringens*.

Suitable enzymes include various BSH enzymes and lipase. BSH is optionally *lactobacillus plantarum* BSH and lipase is optionally animal (eg. mammalian, human) lipase. The *L. plantarum* BSH nucleotide sequence is found in SEQ. ID. NO. 1 (Accession No. A24002) and the corresponding amino acid sequence is found in SEQ. ID. NO. 2 (Accession No. CAA01703). Alternatively, BSH is *Bifidobacterium bifidum, Lactobacillus acidophilus*, and *Clostridium perfringens*. The *Bifidobacterium bifidum* BSH nucleotide sequence is found in SEQ. ID. NO. 9 (Accession No. AY506536) and the corresponding amino acid sequence is found in SEQ. ID. NO. 10 (Accession No. AAR39453). The *Lactobacillus acidophilus* BSH nucleotide sequence is found in SEQ. ID. NO. 5 (Accession No. AF091248) and the corresponding amino acid sequence is found in SEQ. ID. NO. 6 (Accession No. AAD03709). The *clostridium perfringens* BSH nucleotide sequence is found in SEQ. ID. NO. 7 (Accession No. U20191) and the corresponding amino acid sequence is found in SEQ. ID. NO. 8 (Accession No. AAC43454). Enzyme is prepared by transcription and translation of an isolated nucleotide sequence or by de novo protein synthesis. Lipase is optionally human lipase. The human lipase nucleotide sequence is found in SEQ. ID. NO. 3 (Accession No. NM_000235) and the corresponding amino acid sequence is found in SEQ. ID. NO. 4 (Accession No. NP_000226).

Those skilled in the art will recognize that the enzyme nucleic acid molecule sequences are not the only sequences, which may be used to make proteins with enzymatic activity. The genetic code is degenerate so other nucleic acid molecules, which encode a polypeptide identical to an amino acid sequence of the present invention, may also be used. The sequences of the other nucleic acid molecules of this invention may also be varied without changing the polypeptide encoded by the sequence. Consequently, the nucleic acid molecule sequences described below are merely illustrative and are not intended to limit the scope of the invention.

The sequences of the invention can be prepared according to numerous techniques. The invention is not limited to any particular preparation means. For example, the nucleic acid molecules of the invention can be produced by cDNA cloning, genomic cloning, cDNA synthesis, polymerase chain reaction (PCR), or a combination of these approaches (Current Protocols in Molecular Biology (F. M. Ausbel et al., 1989).). Sequences may be synthesized using well-known methods and equipment, such as automated synthesizers.

The invention includes modified nucleic acid molecules with a sequence identity at least about: >17%, >20%, >30%, >40%, >50%, >60%, >70%, >80% or >90% more preferably at least about >95%, >99% or >99.5%, to a DNA sequence in SEQ. ID. NO. 1, 3, 5, 7 or 9 (or a partial sequence thereof). Preferably about 1, 2, 3, 4, 5, 6 to 10, 10 to 25, 26 to 50 or 51 to 100, or 101 to 250 nucleotides or amino acids are modified. Identity is calculated according to methods known in the art. Sequence identity is most preferably assessed by the algorithm of the BLAST version 2.1 program advanced search. Identity is calculated according to methods known in the art. Sequence identity (nucleic acid and protein) is most preferably assessed by the algorithm of BLAST version 2.1 advanced search. BLAST is a series of programs that are available online at http://www.ncbi.nlm.nih.gov/BLAST. The advanced blast search (http://www.ncbi.nlm.nih.gov/blast/blast.cgi?Jform=1) is set to default parameters. (ie Matrix BLOSUM62; Gap existence cost 11; Per residue gap cost 1; Lambda ratio 0.85 default). References to BLAST searches are: Altschul, S. F., Gish, W., Miller, W., Myers, E. W. & Lipman, D. J. (1990) "Basic local alignment search tool." J. Mol. Biol. 215:403410; Gish, W. & States, D. J. (1993) "Identification of protein coding regions by database similarity search." Nature Genet. 3:266272; Madden, T. L., Tatusov, R L. & Zhang, J. (1996) "Applications of network BLAST server" Meth Enzymol. 266:131_141; Altschul, S. F., Madden, T. L., Schäffer, A. A., Zhang, J., Zhang, Z., Miller, W. & Lipman, D. J. (1997) "Gapped BLAST and PSI_BLAST: a new generation of protein database search programs." Nucleic Acids Res. 25:33893402; Zhang, J. & Madden, T. L. (1997) "PowerBLAST: A new network BLAST application for interactive or automated sequence analysis and annotation." Genome Res. 7:649656.

Nucleotide sequences functionally equivalent to BSH (SEQ. ID. NO. 1, 5, 7 and 9) or lipase (SEQ. ID. NO. 3) can occur in a variety of forms as described below. Polypeptides having sequence identity may be similarly identified.

The polypeptides encoded by the BSH or lipase nucleic acid molecules in other species will have amino acid sequence identity at least about: >20%, >25%, >28%, >30%, >40% or >50% to an amino acid sequence shown in SEQ. ID. NO. 2, 4, 6, 8 or 10 (or a partial sequence thereof). Some species may have polypeptides with a sequence identity of at least about: >60%, >70%, >80% or >90%, more preferably at least about: >95%, >99% or >99.5% to all or part of an amino acid sequence in SEQ. ID. NO. 2, 4, 6, 8 or 10 (or a partial sequence thereof). Identity is calculated according to methods known in the art. Sequence identity is most preferably assessed by the BLAST version 2.1 program advanced search (parameters as above). Preferably about: 1, 2, 3, 4, 5, 6 to 10, 10 to 25, 26 to 50 or 51 to 100, or 101 to 250 nucleotides or amino acids are modified.

The invention includes nucleic acid molecules with mutations that cause an amino acid change in a portion of the polypeptide not involved in providing bile acid degrading/ triglyceride degrading activity or an amino acid change in a portion of the polypeptide involved in providing enzymatic activity so that the mutation increases or decreases the activity of the polypeptide.

Other functional equivalent forms of the enzyme nucleic acid molecules encoding nucleic acids can be isolated using conventional DNA-DNA or DNA-RNA hybridization techniques. These nucleic acid molecules and the enzyme sequences can be modified without significantly affecting their activity.

The present invention also includes nucleic acid molecules that hybridize to BSH or lipase sequences (or a partial sequence thereof) or their complementary sequences, and that encode peptides or polypeptides exhibiting substantially equivalent activity as that of a BSH or lipase polypeptide produced by the DNA in SEQ. ID. NO. 1, 3, 5, 7 or 9. Such nucleic acid molecules preferably hybridize to all or a portion of the sequence or its complement under low, moderate (intermediate), or high stringency conditions as defined herein (see Sambrook et al. (most recent edition) Molecular Cloning: A Laboratory Manual, Cold Spring Harbor Laboratory Press, Cold Spring Harbor, N.Y.; Ausubel et al. (eds.), 1995, Current Protocols in Molecular Biology, (John Wiley & Sons, NY)). The portion of the hybridizing nucleic acids is typically at least 15 (e.g. 20, 25, 30 or 50) nucleotides in length. The hybridizing portion of the hybridizing nucleic acid is at least 80% e.g. at least 95% or at least 98% identical to the sequence or a portion or all of a nucleic acid encoding a BSH or lipase polypeptide, or its complement. Hybridizing nucleic acids of the type described herein can be used, for example, as a cloning probe, a primer (e.g. a PCR primer) or a diagnostic probe. Hybridization of the oligonucleotide probe to a nucleic acid sample typically is performed under stringent conditions. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g. SSC or SSPE). Then, assuming that 1% mismatching results in a 1 degree Celsius decrease in the Tm, the temperature of the final wash in the hybridization reaction is reduced accordingly (for example, if sequences having greater than 95% identity with the probe are sought, the final wash temperature is decreased by 5 degrees Celsius). In practice, the change in Tm can be between 0.5 degrees Celsius and 1.5 degrees Celsius per 1% mismatch. Low stringency conditions involve hybridizing at about: 1×SSC, 0.1% SDS at 50° C. for about 15 minutes. High stringency conditions are: 0.1×SSC, 0.1% SDS at 65° C. for about 15 minutes. Moderate stringency is about 1×SSC 0.1% SDS at 60 degrees Celsius for about 15 minutes. The parameters of salt concentration and temperature can be varied to achieve the optimal level of identity between the probe and the target nucleic acid.

The present invention also includes nucleic acid molecules from any source, whether modified or not, that hybridize to genomic DNA, cDNA, or synthetic DNA molecules that encode the amino acid sequence of a BSH or lipase polypeptide, or genetically degenerate forms, under salt and temperature conditions equivalent to those described in this application, and that code for a peptide, or polypeptide that has bile acid degrading/triglyceride degrading activity. Preferably the polypeptide has the same or similar activity as that of a BSH or lipase polypeptide.

The invention also includes nucleic acid molecules and polypeptides having sequence similarity taking into account conservative amino acid substitutions. Changes in the nucleotide sequence which result in production of a chemically equivalent or chemically similar amino acid sequence are included within the scope of the invention. Variants of the polypeptides of the invention may occur naturally, for example, by mutation, or may be made, for example, with polypeptide engineering techniques such as site directed mutagenesis, which are well known in the art for substitution of amino acids. For example, a hydrophobic residue, such as glycine can be substituted for another hydrophobic residue such as alanine. An alanine residue may be substituted with a more hydrophobic residue such as leucine, valine or isoleucine. A negatively charged amino acid such as aspartic acid may be substituted for glutamic acid. A positively charged amino acid such as lysine may be substituted for another positively charged amino acid such as arginine.

Therefore, the invention includes polypeptides having conservative changes or substitutions in amino acid sequences. Conservative substitutions insert one or more amino acids, which have similar chemical properties as the replaced amino acids. The invention includes sequences where conservative substitutions are made that do not destroy bile acid degrading/ triglyceride degrading activity.

Polypeptides comprising one or more d-amino acids are contemplated within the invention. Also contemplated are polypeptides where one or more amino acids are acetylated at the N-terminus. Those of skill in the art recognize that a variety of techniques are available for constructing polypeptide mimetics with the same or similar desired bile acid degrading activity as the corresponding polypeptide compound of the invention but with more favorable activity than the polypeptide with respect to solubility, stability, and/or susceptibility to hydrolysis and proteolysis. See, for example, Morgan and Gainor, Ann. Rep. Med. Chem., 24:243-252 (1989). Examples of polypeptide mimetics are described in U.S. Pat. No. 5,643,873. Other patents describing how to make and use mimetics include, for example in, U.S. Pat. Nos. 5,786,322, 5,767,075, 5,763,571, 5,753,226, 5,683,983, 5,677,280, 5,672,584, 5,668,110, 5,654,276, 5,643,873. Mimetics of the polypeptides of the invention may also be made according to other techniques known in the art. For example, by treating a polypeptide of the invention with an agent that chemically alters a side group by converting a hydrogen group to another group such as a hydroxy or amino group. Mimetics preferably include sequences that are either entirely made of amino acids or sequences that are hybrids including amino acids and modified amino acids or other organic molecules.

The invention also includes polypeptide fragments of the polypeptides of the invention which may be used to confer bile acid degrading activity if the fragments retain activity. The invention also includes polypeptide fragments of the polypeptides of the invention which may be used as a research tool to characterize the polypeptide or its activity. Such polypeptides preferably consist of at least 5 amino acids. In preferred embodiments, they may consist of 6 to 10, 11 to 15, 16 to 25, 26 to 50, 51 to 75, 76 to 100 or 101 to 250 amino acids of the polypeptides of the invention (or longer amino acid sequences). The fragments preferably have bile acid degrading/triglyceride degrading activity.

Known techniques are used to bind enzyme or bacteria to a support, such as a polymer bead. In short, the technique optionally involves simple immobilization/entrapment of the enzyme molecules in a support system like polymers. The support or bead may be made from solid or semi-solid material. It may also be a porous support, hollow support or a continuous support (without pores or hollows).

The immobilized biological active agent is optionally encapsulated or microencapsulated. Encapsulation is a term used to include the methods of both macroencapsulation and microencapsulation. The term microencapsulation refers to a subclass of encapsulation, where small, microencapsulated capsules are produced. Encapsulation and microencapsulation techniques are known in the art. Microcapsules are small spherical containers or coated tissues in the 0.3-1.5 mm range, whereas macrocapsules are larger flat-sheet or hollow-fiber membraned vessels. Both macro- and microcapsules must contain a cellular environment that is able to support cellular metabolism and proliferation, as the cells they accommodate provide the capsule functionality.

Artificial cell microencapsulation is a technique used to encapsulate biologically active materials in specialized ultra thin semi-permeable polymer membranes (Chang and Prakash, 1997; Chang, 1964). Methods for preparing artificial cells have been well documented in the pertinent art. Artificial cell membranes are optionally selected or designed for each specific therapeutic device by one of skill in the art, because one may engineer several different membranes for artificial cell preparations with required membrane properties for a desired application. The use of different membranes allows for variation in permeability, mass transfer, mechanical stability, buffering capability, biocompatibility, and other characteristics. A balance has to be maintained among the physical properties of capsule membranes so as to support the entrapped cell's survival.

The mass transport properties of a membrane are critical since the influx rate of molecules, essential for cell survival, and the outflow rate of metabolic waste ultimately determines the viability of entrapped cells. Any barriers can be potentially applied to enzyme applications. Ordinarily the desired capsule permeability is determined by the molecular weight cut-off (MWCO), and is application dependent. The MWCO is the maximum molecular weight of a molecule that is allowed passage through the pores of the capsule membrane (Uludag et al. (2000) *Adv. Drug Deliv. Rev.* 42:29-64). For transplantation, the MWCO must be high enough to allow passage of nutrients, but low enough to reject antibodies and other immune system molecules. The MWCO range is optionally 3000 D to 950,000 D (Chang and Prakash, 1998). The MWCO of orally delivered microcapsules must allow for the passage of unwanted metabolites from the plasma into the microcapsule, and then must either facilitate the subsequent removal of the altered molecule or provide for its storage (Uludag et al., 2000). For cells of the invention that are to be administered orally or implanted in the gastrointestinal tract, one optionally uses a retainer that allows passage of nutrients, but blocks antibodies and other immune molecules, for example a semi-permeable membrane having a MWCO 3000 D to 950,000 D (Chang and Pralcash, 1998). Alternatively, the lower end of the range may be about: 2000 D, 4000 D, 5000 D or 10,000 D and the higher end of the range may be about: 900,000 D, 750,000 D or 500,000 D.

The most common type of membrane used for cell therapy is the single alginate based polymer membrane; however, several other substances may be used such as various proteins, polyhemoglobin, and lipids (Uludag et al., 2000; Prakash and Jones, 2002). Yet another approach for membrane composition is to use a biodegradable synthetic polymer such as polylactide, polyglycolic acid, and polyanhydride. Commonly used membranes include hollow fiber Membranes, alginate-polylysine-alginate (APA) membrane, cellulose nitrate, polyamide, lipid-complexed polymer, and lipid vesicles. Established and promising polymers for live cell encapsulation and enzyme encapsulation include alginate-polylysine-alginate (APA), alginate-polymethylene-co-guanidine-alginate (A-PMCG-A), hydroxymethylacrylate-methyl methacrylate (HEMA-MMA), Multilayered HEMA-MMA-MAA, polyacrylonitrilevinylchloride (PAN-PVC), acrylonitirle/sodium methallylsuflonate (AN-69), polyethylene glycol/poly pentamethylcyclopentasiloxane/polydimethylsiloxane (PEG/PD$_5$/PDMS), poly N/N-dimethyl acrylamide (PDMAAm), Siliceous encapsulates, and cellulose sulphate/sodium alginate/polymethylene-co-guanidine (CS/A/PMCG) (with permission from Satya Prakash and Hahn Soe-Lin, unpublished work). Other materials that are useful include cellulose acetate phthalate, calcium alginate and k-carrageenan-Locust bean gum gel beads, gellan-xanthan beads, poly(lactide-co-glycolides), carageenan, starch polyanhydrides, starch polymethacrylates, polyamino acids, enteric coating polymers.

The design of a membrane, intended for use in oral live cell therapy or enzyme therapy, must take into consideration several primary factors so as to minimize microbial death and maximize therapeutic effectiveness. To assure their efficacy, artificial cells intended for oral administration, must be designed to protect their living cargo against both the acidic environment of the stomach and immunoglobulin released by the intestinal immune response.

A useful formulation is the encapsulation of calcium alginate beads with poly-L-lysine (PLL) forming alginate-poly-L-lysine-alginate (APA) microcapsules. In the APA membrane microcapsule, alginate forms the core and matrix for the cell and PLL binds to the alginate core. Binding of PLL to alginate is the result of numerous long-chain alkyl-amino groups within PLL that extend from the polyamide backbone in a number of directions and interact with various alginate molecules, through electrostatic interactions. The resulting cross-linkage produces a stable complex membrane that reduces the porosity of the alginate membrane and forms an immunoprotective barrier.

Alternatively, Alginate/Poly-l-lysine/Pectin/Poly-l-lysine/Alginate (APPPA), Alginate/Poly-l-lysine/Pectin/Poly-l-lysine/Pectin (APPPP), and Alginate/Poly-L-lysine/Chitosan/Poly-l-lysine/Alginate (APCPA) membranes is used for encapsulation. It has been shown that these multi-layer membrane formulations perform well in GI stability tests, providing for increased resistance to complete dissolution in water, dilute acids and base, as well as in the presence of ion chelators, while allowing for more precise control over membrane permeability (Ouyang et al., 2002; Chen et al., 2002).

There are various methods available for preparing artificial cells containing live cells for therapy. For example, for preparation of the classic alginate-polylysine-alginate (APA) membrane, the live cells, such as bacterial cells, are suspended in a matrix of the natural polymer alginate (1.5%). The viscous polymer-bacterial suspension is passed through a 23-gauge needle using a syringe pump. Sterile compressed air, passed through a 16-gauge coaxial needle, is then used to shear the droplets coming out of the tip of the 23-gauge needle. The droplets are allowed to gel for 15 minutes in a gently stirred ice-cold solution of solidifying chemicals, such as $CaCl_2$ (1.4%). After gelation in the $CaCl_2$, the beads are then washed with HEPES (0.05% in HEPES, pH 7.20), coated with polylysine (0.1% for 10 min) and washed again in HEPES (0.05% in HEPES, pH 7.20). The resultant capsules are then coated by reaction with alginate (0.1% for 10 min) and washed with appropriate chemicals to dissolve their inner core content. For this step a 3.00% citrate bath (3.00% in 1:1 HEPES-buffer saline, pH 7.20) is often used. The microcapsules formed can then be stored at 4° C. in minimal solution (10% cell nutrient to 90% water).

In one embodiment, the carrier is intended for oral administration and is optionally in the form of a nutraceutical or functional food product. "Nutraceutical" means a product isolated or purified from foods (or sources used to make food, such as plants, animals or other organisms) that is generally sold in a medicinal form not usually associated with food. A nutraceutical is demonstrated to have a physiological benefit or provide protection against chronic disease. "Functional Food Product" means it is similar in appearance to or may be a conventional food, is consumed as part of a usual diet and is demonstrated to have physiological benefits and/or reduce the risk of chronic disease beyond basic nutritional functions.

In another embodiment, the carrier is an implantation device. For example, it is useful when administered to an appropriate place in the GI tract using implantable bags/pouches. Implantation of artificial cells has been described for the treatment of many disorders including hepatic failure, pancreatic failure (Type I child onset diabetes), and alpha-1-antitrypsin deficiency (Moraga et al., 2001; Ambrosino et al., 2003). The procedure is common and known to one skilled in the art of cell transplantation. To summarize, the capsules are inserted into the peritoneal cavity and interface with the visceral circulation. The capsules can then be retrieved.

Unwanted intraluminal bile acids in the gastrointestinal system is associated with defective ileal transport of bile acids due to a congenital defect, resection of the ileum or bowel diseases. "Defective ileal transport" means that there is excessive bile flow into the blood. Accordingly, the present invention provides a method for lowering of intraluminal bile acid of patients suffering from defective ileal transport of bile acids due to a congenital defect, resection of the ileum or a bowel disease, which comprises of administering a bile acid lowering amount of a composition of the present invention.

The present inventors have demonstrated that microencapsulated cells, such as bacteria expressing BSH, can degrade bile salts. Accordingly, the present invention provides a method for lowering of serum cholesterol of an animal, which comprises a bile acid lowering amount of a composition of the present invention. In another embodiment, the invention provides a method for preventing or treating any disease or disorder characterized by cholesterol or having excessive cholesterol as a risk factor comprising administering a bile acid lowering amount of a composition of the present invention. Cholesterol disorders include familial hypercholesterolemia or inherited cholesterol disorder (ICD), defects in the gene products of cholesterol metabolism e.g. 7-alpha-hydroxylase, and various forms of xanthomas. Increased levels of serum cholesterol may indicate atherosclerosis, biliary cirrhosis, familial hyperlipidemias, high-cholesterol diet, hypothyroidism, myocardial infarction, nephritic syndrome and uncontrolled diabetes. "Excessive cholesterol" means outside the optimal cholesterol range. Optimal cholesterol level is less than 200 mg/dL. Borderline High is 200-239 mg/dL and anything over 240 mg/dL is high. (http://www.nhlbi.nih.gov/health/public/heart/chol/wynt-k.htm). The National Cholesterol Education Program NCEP III report on cholesterol (http://www.nhlbi.nih.gov/guidelines/cholesterol/) includes "Full Report" and a "Drug Therapy" section. This provides a review of examples of cholesterol management by statins, bile acid sequestrants, diet, etc. and it relates to cholesterol levels and risk factors (eg. see Tables IV.1-1 VI.1-1; VI.1-2, VI.1-3). The present invention drug is similar to bile acid sequestrants. The NCEP report provides guidance on use of pharmaceutical therapy in relation to the presence of other risk factors. There are two types of cholesterol, HDL cholesterol (sometimes called good cholesterol) and LDL cholesterol (sometimes called bad cholesterol). "Excessive cholesterol" may also be determined with respect to LDL. For example, drug therapy is optionally considered for individuals with multiple risk factors (2 or more) when LDL cholesterol is: >100 mg/dL (eg. with a goal to reduce LDL cholesterol to <100 mg/dL), at least 130 mg/dL (eg. with a goal to reduce LDL cholesterol to less than 130 mg/dL), at least 160 mg/dL (eg. with a goal to reduce LDL cholesterol to less than 130 mg/dL). Furthermore, drug therapy is also optionally considered for individuals with 0-1 risk factors when LDL cholesterol is at least 190 mg/dL (eg. with a goal to reduce LDL cholesterol to less than 160 mg/dL). Normal values tend to increase with age, and premenopausal women have somewhat lower levels than men of the same age.

The composition for lowering of intraluminal bile acids or serum cholesterol may be administered singly or in combination with another cholesterol lowering therapeutic. Another cholesterol lowering therapeutic includes BAS Cholestyramine resin (Locholest, Questran), Colesevelam (WelChol), Colestipol (Colestid), lovastatin (Mevacor), pravastatin (Pravachol), zocor (Zocor), fluvastatin (Lescol) and atorvastatin (Lipitor), probiotic formulations containing other live bacterial cells and neutraceuticals and natural cholesterol lowering products such as carbohydrates.

In another embodiment, the present invention provides a method for lowering of serum cholesterol and/or total body cholesterol of animals for the purpose of producing animal products of reduced cholesterol content, which comprises administering a bile acid lowering amount of a composition of the present invention. Animal products optionally include cow, pig, or poultry meat or products such as eggs and milk.

Colon cancer has been linked to diet and the proposed mechanism is that a high fat diet leads to an increased secretion of primary bile salts into the small intestine. The increased biliary secretion leads to the formation of higher levels of deconjugated bile acids that may then exert their cytotoxic and mutagenic effect on the gastrointestinal mucosa (Oumi and Yamamoto, 2000). It is these conjugated bile salts which have been incriminated in colonic carcinogenesis and thus a system for their removal would be a valuable tool for the prevention of colon cancer. Accordingly, the present invention provides a method for (preventing or treating) colon cancer in a patient, which comprises administering a bile acid lowering amount of a composition of the present invention.

In one embodiment, the present invention provides a method for quantitatively measuring bile acids or triglycerides.

Urinary levels of sulfated bile acids are known to be significantly elevated in liver disease and hepatobiliary disease. Accordingly, the present invention provides an in vitro diagnostic tool for liver or hepatobiliary diseases in a patient, which comprises
   a) support;
   b) at least one biologically active agent immobilized onto said support;
wherein the immobilized agent allows detection and/or measurement of bile acid degradation when contacted with a biological sample. The biologically active agent may be any cell expressing or capable of expressing a bile degrading enzyme, anaerobic bacteria expressing or capable of expressing a bile degrading enzyme, a bile degrading enzyme-containing cell extract or a bile degrading enzyme. The support optionally comprises a support means. The present invention also provides an in vitro diagnostic tool for steathorrea in a patient which comprises:
   a) a support;
   b) a biologically active agent immobilized onto said support;
wherein the immobilized agent allows detection and/or measurement of triglyceride degradation when contacted with a biological sample.

The biological sample is optionally urine. Alternatively, the biological sample is blood, feces or vomit. The detection of bile acid/triglyceride degradation is based on an indicator that changes colour. Alternatively, the detection measures the quantity of bile acid/triglyceride degradation. Bile degrading enzyme includes BSH. BSH is optionally *lactobacillus plantarum* BSH. The *L. plantarum* BSH nucleotide sequence is found in SEQ. ID. NO. 1 (Genbank Accession No. A24002) and the corresponding amino acid sequence is found in SEQ. ID. NO. 2 (Genbank Accession No. CAA01703). Alternatively, BSH is *Bifidobacterium bifidum, Lactobacillus acidophilus*, or *Clostridium perfringens*. The *Bifidobacterium bifidum* BSH nucleotide sequence is found in SEQ. ID. NO. 9 (Genbank Accession No. AY506536) and the corresponding amino acid sequence is found in SEQ. ID. NO. 10 (Genbank Accession No. AAR39453). The *Lactobacillus acidophilus* BSH nucleotide sequence is found in SEQ. ID. NO. 5 (Genbank Accession No. AF091248) and the corresponding amino acid sequence is found in SEQ. ID. NO. 6 (Genbank Accession No. AAD03709). The *clostridium perfringens* BSH nucleotide sequence is found in SEQ. ID. NO. 7 (Genbank Accession No. U20191) and the corresponding amino acid sequence is found in SEQ. ID. NO. 8 (Genbank Accession No. AAC43454). Triglyceride degrading enzyme includes lipase. The human lipase nucleotide sequence is found in SEQ. ID. NO. 3 (Accession No. NM_000235) and the corresponding amino acid sequence is found in SEQ. ID. NO. 4 (Accession No. NP_000226). Enzyme is prepared by transcription and translation of an isolated nucleotide sequence or by de novo protein synthesis.

Cells or bacteria may be genetically engineered or produced by other methods, such as irradiation-induced mutation or selection of naturally mutated cells that degrade increased amounts of bile acid/triglyceride compared to a wild type cell. The cells are optionally any cell, such as an animal cell (eg. human cell) or a fungal cell or a bacterial cell as long as they are capable of expressing the enzyme. The bacteria is optionally *Lactobacillus* preferably, *Lactobacillus plantarum, Lactobacillus reuteri* or a combination thereof. The bacteria is optionally *Bifidobacterium bifidum, Lactobacillus acidophilus*, and *clostridium perfringens*.

The liver is a complex organ with interdependent metabolic, excretory, and defense functions. No single or simple test assesses overall liver function; sensitivity and specificity are limited. Use of several screening tests improves the detection of hepatobiliary abnormalities, helps differentiate the basis for clinically suspected disease, and determines the severity of liver disease. Accordingly, in a further embodiment, the present invention provides an in vitro method for measuring bile acid which comprises
   (a) contacting a biological sample with a tool of the present invention,
   (b) contacting a control sample with a tool of the present invention,
   (c) comparing the amount of degradation of bile acid in (a) to (b), wherein a higher level of degradation product in (a) than (b) is indicative of a liver or hepatobiliary disease.

For example, the degradation product may be at least 10%, at least 30%, at least 50% or at least 100% higher. In one embodiment, the biological sample is urine. Alternatively, the biological sample is feces, vomit or blood. Elevated urinary bile acid levels can occur in infants and adults, for example, in hepatobiliary diseases including hepatitis A, B, C, G, Infantile obstructive cholangiopathy, Autoimmune hepatitis, Neonatal hepatitis, Infantile obstructive cholangiopathy, Progressive familial intrahepatic cholestasis (PFIC) and Intrahepatic cholestasis. Infants can also have bileary atresia as seen in the article by Toshihiro Muraji et al. 2003. Elevated levels of sulfated bile acid (USBA) ranged from 9.1 to 341.0 µmol/L (92.3±141.1). USBA is not normally seen in urine. Liver or hepatobiliary disease also includes flumanant hepatic failure, general liver disease, gallstone disease and primary biliary cirrhosis.

The present invention also provides an in vitro method for measuring triglyceride comprising:
   a) contacting a biological sample with a tool of the present invention
   b) contacting a control sample with a tool of the present invention
   c) comparing the amount of degradation of triglyceride in (a) and (b)
wherein a higher level of degradation product in (a) than (b) is indicative of high triglyceride fat content.

The pharmaceutical compositions of the invention can be administered to humans or animals by a variety of methods including, but not restricted to topical administration, oral administration, aerosol administration, intratracheal instillation, intraperitoneal injection, injection into the cerebrospinal fluid, and intravenous injection in methods of medical treatment involving bile acid degrading activity. Dosages to be administered depend on patient needs, on the desired effect and on the chosen route of administration.

The pharmaceutical compositions can be prepared by known methods for the preparation of pharmaceutically acceptable compositions which can be administered to patients, and such that an effective quantity of the cell or enzyme is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA).

The methods of combining the active molecules with the vehicles or combining them with diluents is well known to those skilled in the art. The composition could include a targeting agent for the transport of the active compound to specified sites within tissue.

The following non-limiting examples are illustrative of the present invention:

MATERIALS AND METHODS

Bacterial Strains and Cell Growth and Selection Conditions

Any cell, such as a bacterial cell, may be engineered to overexpress BSH or lipase as described in the application and using known techniques. Two suitable bacterial strains used were the bile salt hydrolytic (BSH) isogenic *Lactobacillus plantarum* 80 (pCBHl) (LP80 (pCBHl)) strain (Christiaens et al., 1992) and the *Lactobacillus reuteri* (*L. reuteri*) strain (De Boever et al., 2000). Overproduction of the BSH enzyme in LP80 (pCBHl) was obtained as described by Christiaens et al., 1992. The BSH overproducing LP80 (pCBHl) strain carried the multicopy plasmid pCBHl which carried the LP80 (pCBHl) chromosomal bsh gene and a marker gene, the erythromycin resistance gene.

The *Lactobacillus* strains are optionally grown in MRS broth at 37° C. in a bench top incubator or in an anaerobic growth cabinet. For the growth of LP80 (pCBHl), the MRS broth was supplemented with 100/µg/ml erythromycin to select for bacteria overexpressing BSH (ie. carrying the multicopy plasmid pCBHl).

Immobilization of Cells—*Lactobacillus Plantarum* 80 (pCBHI) and/or *Lactobacillus reuteri*

50 ml of 1.5% low viscosity alginate solution was prepared and filtered through a 0.22 µm filter into a sterile 60 ml syringe. LP80 (pCBHl) was grown at 37° C. in MRS broth and prepared as a concentrated microorganism suspension by re-suspension of microorganism in 10 ml of sterilized physiologic solution. *L. reuteri* was grown at 37° C. in MRS 10 broth and was added to the LP80 (pCBHl) concentrated microorganism suspension. The 10 ml concentrated microorganism suspension was added to the 50 ml low viscosity alginate solution and mixed well. The alginate/microorganism mixture was immobilized, through a 300 µm nozzle, into a filtered solution of CaCl with an encapsulator. This procedure is optionally performed in a biological containment hood to assure sterility. The immobilized cultures was stored in 1.0 L minimal solution (10% MRS and 90% Physiologic Solution) at 4° C.

Microencapsulation of *Lactobacillus Plantarum* 80 (pCBHl) and/or *Lactobacillus reuteri*

The microencapsulation procedure followed the same steps as the immobilization procedure described above with the addition of the following steps. The immobilized LP80 (pCBHl) and *L. reuteri* alginate beads were washed in autoclaved physiological solution (8.5 NaCl/L), placed in a 1% solution of poly-L-lysine for 10 min., washed in physiological solution, placed in 1% solution of low-viscosity alginate for 10 min. and washed in physiological solution a final time. This procedure was performed in a biological containment hood to assure sterility. The microencapsulated LP80 (pCBHl) (FIG. 1) and *L. reuteri* was then stored in 1.0 L minimal solution (10% MRS and 90% Physiologic Solution) at 4° C.

Microencapsulation and/or Immobilization of Bile Salt Hydrolase (BSH) Enzyme

The microencapsulation and immobilization procedures for the free BSH enzyme followed the same steps as outlined in the procedures described above with the following changes. The free enzyme was added to a physiological solution or was simply added to the alginate preparation prior to bead formation. This procedure was performed in a biological containment hood to assure sterility. The microencapsulated enzyme was then stored in 1.0 L minimal solution (10% MRS and 90% Physiologic Solution) at 4° C.

BSH Activity of Immobilized *Lactobacillus Plantarum* 80 (pCBHl) Alginate Beads

To investigate the BSH activity of the immobilized BSH overproducing LP80 (pCBHl), batch experiments were performed. Five grams cell dry weight (CDW) of immobilized LP80 (pCBHl) was added to fresh MRS broth to which 10.0 mM GDCA and 5.0 mM TDCA were added. Samples were taken at regular time intervals during the 24 h incubation to determine the bile salt concentration in the reaction vessels.

BSH Activity of Lactobacillus Plantarum 80 (pCBHI) Microcapsules

To investigate the BSH activity of the microencapsulated BSH overproducing LP80 (pCBHl), batch experiments were performed. Five grams cell dry weight (CDW) of microencapsulated LP80 (pCBHl) was added to fresh MRS broth to which 10.0 mM GDCA and 5.0 mM TDCA were added. Samples were taken at regular time intervals during the 24 h incubation to determine the bile salt concentration in the reaction vessels.

Bile Salt Hydrolase Assay

A modification of the HPLC-procedure described by Scalia (1988) was used to determine BSH activity. Traditionally, in vitro bile acid experimentation has involved the use of HPLC to determine the quantity of various tauro- and glycol-bile acids in complex mixtures of added bile acids in complex aqueous media (Scalia, 1988; Cantafora et al, 1987; Coca et al., 1994). Methods to separate such mixtures have required a lengthy workup involving a (1:4; v:v) sample:isopropanol extraction followed by evaporation and resuspension steps (Scalia, 1988; Cantafora et al, 1987; Coca et al., 1994; De Smet et al., 1994). While this method can produce, accurate results, the time consuming and labor intensive workup step of evaporation was eliminated, allowing for an efficient workup while preserving the quality of bile acid separation and quantification (Jones et al., 2003).

Analyses were performed on a reversed-phase C-18 column: LiChrosorb™ RP 18, 5 µm, 250×4.6 mm from HiChrom™ (Novato, Calif., USA). The HPLC system was made up of two ProStar™ 210/215 solvent delivery modules, a ProStar™ 320 UV/Vis Detector, a ProStar™ 410 AutoSampler™, and Star LC Workstation Version 6.0 software was used. The solvents used were HPLC-grade methanol (solvent A), and solvent B, which was acetate buffer prepared daily with 0.5 M sodium acetate, adjusted to pH 4.3 with o-phosphoric acid, and filtered through a 0.22 µm filter. An isocratic elution of 70 percent solvent A and 30 percent solvent B was used at a flow rate of 1.0 ml/min at room temperature. An injection loop of 20 µl was used, and the detection occurred at 205 nm within 25 min after injection of the bile salt extract.

Quarter ml samples to be analyzed were acidified by the addition of 2.5 µl of 6 N HCl to stop any further enzymatic activity. A modification of the extraction procedure described by Cantafora was used (Cantafora et al., 1987; Jones et al., 2003). From the 0.25 ml sample, bile salts were extracted using a solution of methanol (1:1; v:v). GCA was added as an internal standard at 4.0 mM. The samples were mixed vigorously for 10 min and centrifuged at 1000 g for 15 min. The supernatant was then filtered through a 0.22 µm syringe driven HPLC-filter and the samples were analyzed directly after filtration.

Preparation of Alginate Beads Containing Immobilized Genetically Engineered *Lactobacillus plantarum* 80 (pCBHI) Cells Alginate beads containing genetically engineered *Lactobacillus plantarum* 80 (pCBHl) cells (FIG. 1) were prepared using the methods described above and were stored at 4° C. for use in experiments. Sterile conditions and procedures were strictly adhered to during the process of microencapsulation.

Figure 2:
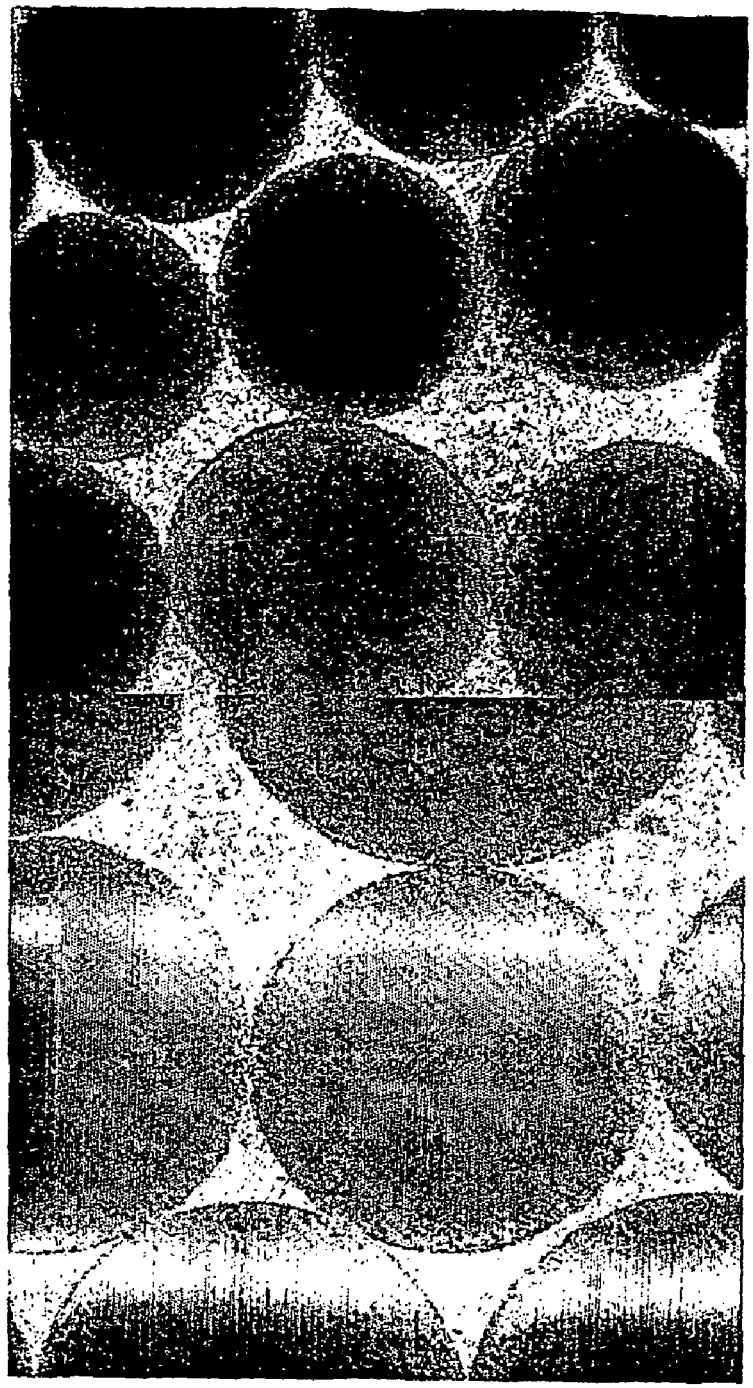
FIG. 2 illustrates a photomicrograph of *Lactobacillus plantarum* 80 (pCBH1) microcapsules at 77× magnification (A) and at 112× magnifications (B)

Preparation of Artificial Cell Microcapsules Containing Genetically Engineered *Lactobacillus plantarum* 80 (pCBHl) Cells Artificial cell microcapsules containing genetically engineered *Lactobacillus plantarum* 80 (pCBHl) cells (FIG. 2) were prepared using the methods described above and were stored at 4° C. for use in experiments. Sterile conditions and procedures were strictly adhered to during the process of microencapsulation.

Determination of Bile Acids by HPLC

Figure 3:
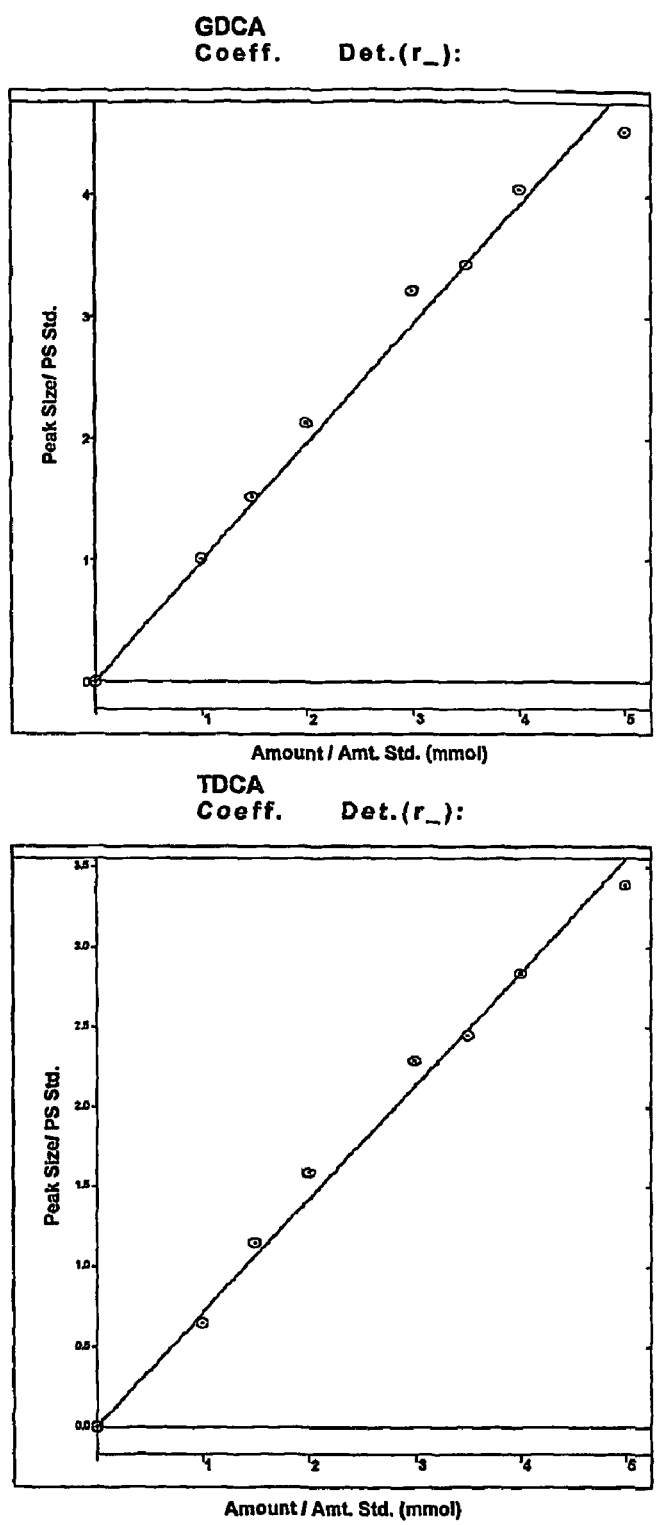
FIG. 3 illustrates HPLC calibration curves for GDCA and TDCA measurements.

To generate a calibration curve for quantifying the HPLC sample results, known quantities of GDCA and TDCA were added to MRS broth and 0.25 mL samples were analyzed using the modified HPLC bile salt hydrolase assay outlined above. FIG. 3 shows the calibration curves for GDCA and TDCA with a 4.0 mM GCA internal standard and correlation factors of 0.987599 and 0.991610 respectively. It is clear that this method allows for the accurate identification and quantitative measurements of various bile acids (Jones et al, 2003).

Results:

EXAMPLE 1

BSH Activity of Alginate Beads Containing Immobilized *Lactobacillus plantarum* 80 (pCBHl)

Figure 4:
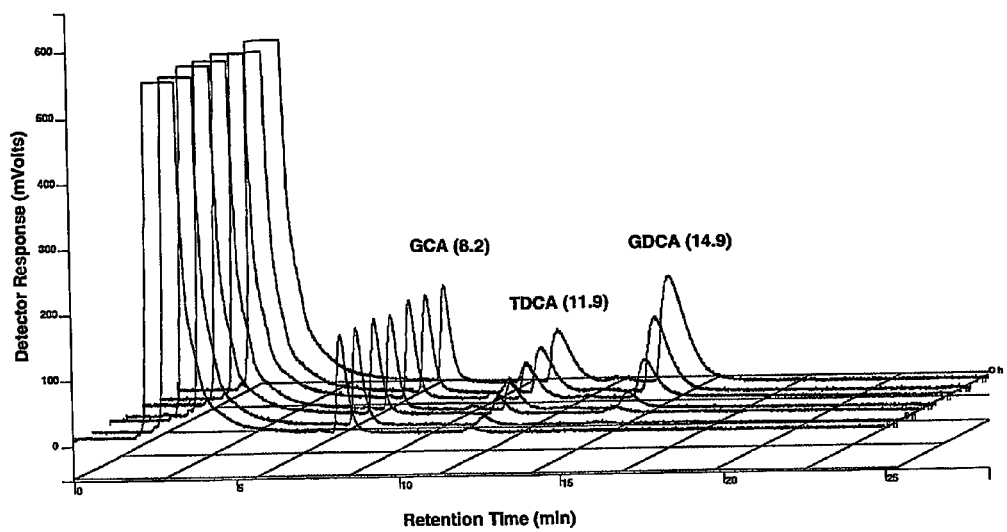
FIG. 4 illustrates overlaid HPLC chromatograms of bile acids in reaction media over time (0 h, 1 h, 2 h, 3 h, 4 h, 5 h, and 6 h). Decreasing peak areas of TDCA and GDCA indicate BSH activity of immobilized *Lactobacillus plantarum* 80 (pCBH1)

To show the BSH activity of alginate beads containing immobilized LP80 (pCBHl), previously stored at 4° C., 5 g CDW of immobilized LP80 (pCBl) was incubated in MRS broth supplemented with 10.0 mM GDCA and 5.0 mM TDCA. The concentration of bile acids was monitored by analyzing media samples at regular intervals over 24 hours. FIG. 4 shows superimposed HPLC chromatograms of bile acids in reaction media taken from one of the experiments at 0 h, 1 h, 2 h, 3 h, 4 h, 5 h, and 6 h. Decreasing peak areas of TDCA and GDCA bile acids indicate BSH activity of alginate beads containing immobilized LP80 (pCBHl). The internal standard was GCA and was the first peak eluted.

EXAMPLE 2

BSH Activity of *Lactobacillus Plantarum* 80 (pCBH1) Microcapsules

Figure 5:
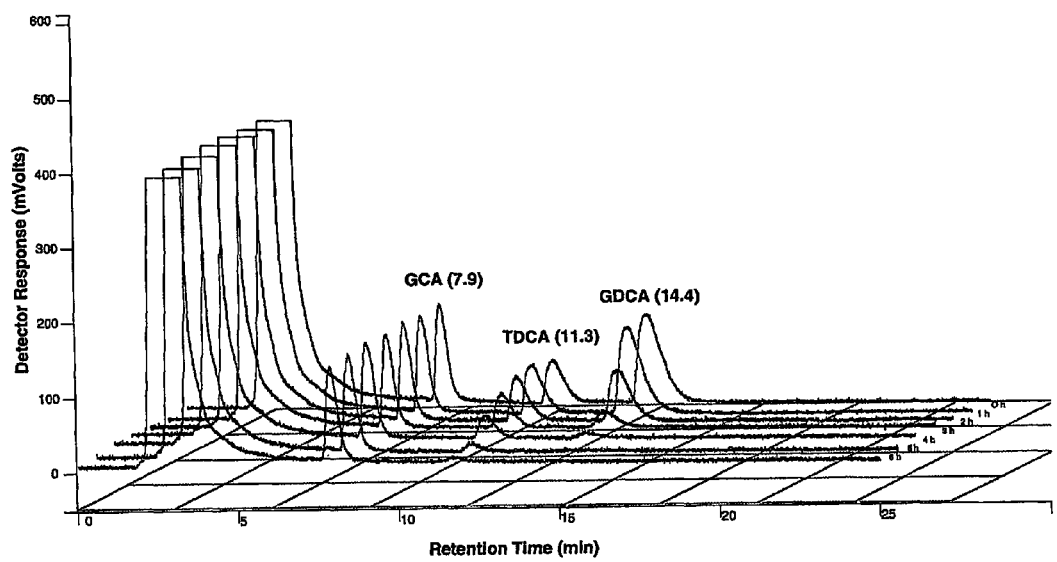
FIG. 5 illustrates overlaid HPLC chromatograms of bile acids in reaction media over time (0 h, 1 h, 2 h, 3 h, 4 h, 5 h, and 6 h). Decreasing peak areas of TDCA and GDCA indicate BSH activity of *Lactobacillus plantarum* 80 (pCBHl) microcapsules.

To show the BSH activity of microencapsulated LP80, previously stored at 4° C., and to show that microencapsulated LP80 (pCBH1) depletes high concentrations of bile acids, 5 g of microencapsulated LP80 (pCBH1) was incubated in MRS broth supplemented with 10.0 mM GDCA and 5.0 mM TDCA. The concentration of bile acids was monitored by analyzing media samples at regular intervals over 12 hours. FIG. 5 shows superimposed HPLC chromatograms of bile acids in reaction media taken from one of the experiments at 0 h, 1 h, 2 h, 3 h, 4 h, 5 h, and 6 h. Decreasing peak areas of TDCA and GDCA bile acids indicate BSH activity of LP80 (pCBHl) microcapsules. The internal standard was GCA and was the first peak eluted.

The BSH activity of 0.25 g CDW of microencapsulated LP80 (pCBHl) and 0.26 g CDW immobilized LP80 (pCBHl), both previously stored at 4° C., was determined and is shown in Table 1. The BSH activity of 0.25 g CDW of microencapsulated LP80 (pCBHl) was calculated based on the depletion of 0.2 mmol of GDCA in a 4 h period, and the BSH activity towards TDCA was based on the breakdown of 0.1 mmol of TDCA in a 5 h period. The BSH activity of 0.26. g CDW of immobilized LP80 (pCBHl) was calculated based on the depletion of 0.2 mmol of GDCA in a 5 h period, and the BSH activity towards TDCA was based on the breakdown of 0.1 mmol of TDCA in a 6 h period. Also, these calculations were based on the in-vitro depletion of bile acids with LP80 (pCBHl) in 5.0 g alginate microcapsules in a complex mixture of the bile acids.

TABLE 1

Bile salt hydrolayse (BSH) activity (μmol DCA/mg CDW/h) of immobilized and microencapsulated *Lactobacillus plantarum* 80 (pCBHl), previously stored at 4° C., towards glyco- and tauro- bile acids.

| Strain | BSH activity (μmol DCA/mg CDW · h) towards | | |
| --- | --- | --- | --- |
|  | GDCA | TDCA | DCA (conjugated) |
| Immobilized LP80 (pCBHl) | 0.17 | 0.07 | 0.24 |
| Micro. LP80 (pCBHl) | 0.19 | 0.08 | 0.27 |

Figure 6:
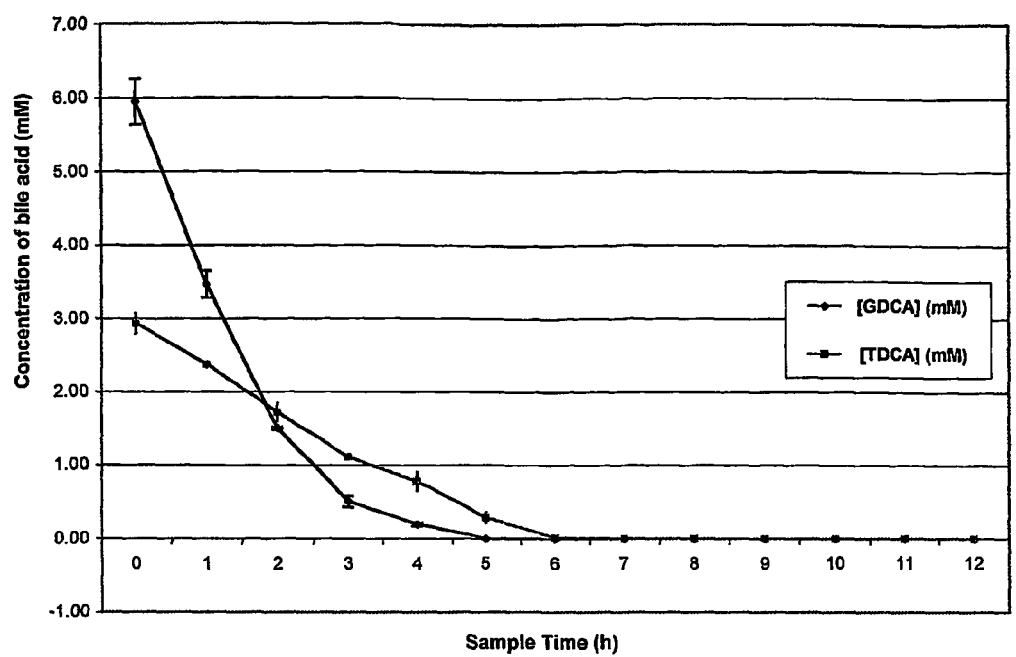
FIG. 6 illustrates BSH activity and GDCA and TDCA depletion efficiency of immobilized *Lactobacillus plantarum* 80 (pCBHl) in an in-vitro experiment. The concentration of GDCA and TDCA bile acids are shown over time. The experiment was performed in triplicate: error bars indicate standard deviations.

FIG. 6 shows the BSH activity of immobilized LP80 (pCBHl) in alginate in an in-vitro bile acid experiment over a 12 h period. The concentration of GDCA and TDCA bile acids are shown to decrease over time. It is clear from FIG. 6 that the BSH activity of immobilized LP80 (pCBHl) began immediately and depleted GDCA at a greater initial rate. While TDCA also began to breakdown immediately, it did so at a slower rate than GDCA. The removal of GDCA, however, experienced concentration effects as it depleted and thus the breakdown of GDCA slowed as the experiment progressed.

Figure 7:
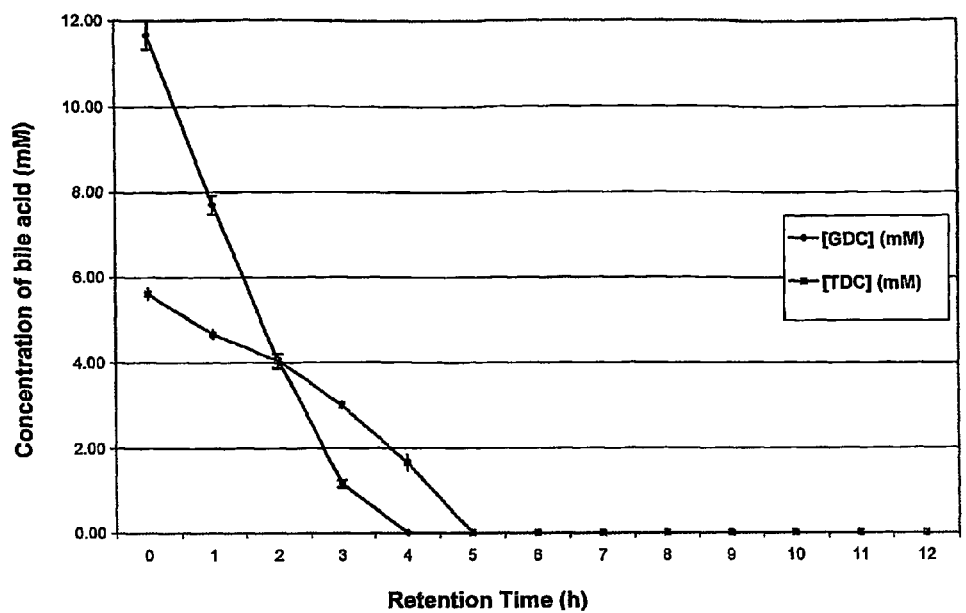
FIG. 7 illustrates BSH activity and GDCA and TDCA depleting efficiency of *Lactobacillus plantarum* 80 (pCBHl) microcapsules in an in-vitro experiment. The concentration of GDCA and TDCA bile acids are shown over time. The experiment was performed in triplicate: error bars indicate standard deviations.

FIG. 7 shows the BSH activity of LP80 (pCBHl) microcapsules in the in-vitro bile acid experiment over a 12 h period. The concentration of GDCA and TDCA bile acids are shown to decrease over time. It is clear from FIG. 7 that the BSH activity of LP80 (pCBHl) began immediately and depleted GDCA at a greater initial rate. While TDCA also began to breakdown immediately, it did so at a slower rate than GDCA. The removal of GDCA, however, experienced concentration effects as it was depleted early and thus the breakdown of GDCA slowed as the experiment progressed and the BSH activity towards TDCA increased.

To show the fate of the products of deconjugation, an experiment was performed using a calibration of increasing concentrations of TDCA, GDCA, and DCA. FIG. 10A shows superimposed HPLC chromatograms of samples at 0 h, 1 h, 2 h, 3 h, 4 h, 5 h, and 6 h. Decreasing peak areas of TDCA and GDCA bile acids indicate BSH activity of microencapsulated LP80 (pCBH1). These results were compared to earlier studies using immobilized beads containing LP80 (pCBH1) (FIG. 10B) Decreasing peak areas of TDCA and GDCA bile acids show BSH activity of alginate beads containing immobilized LP80 (pCBH1). The peak detected just before the measured TDCA peak was diminished totally within 4 h and corresponds to the calibration peak of DCA. The absence of a corresponding peak in the encapsulation results shows the clear advantage of using encapsulated cells.

EXAMPLE 3

Experimental Rat Model and In-Vivo Experimental Procedure

The in-vivo animal study employs young male Wistar rats and shows the suitability of the microcapsule formulation for oral delivery of live genetically engineered LP80 cells and the efficacy of such encapsulated bacteria in lowering total cholesterol and improving the lipid profile. A standard procedure (Usman & Hosono, 2000) for making an elevated blood serum cholesterol rat model by feeding a cholesterol-rich diet is used. Although some effective CHD rat models exist, a model involving manual elevation of blood serum levels provides greater flexibility in controlling cholesterol.

For the in-vivo experimental protocol, 24 Wistar rats (Charles River Laboratories, USA), aged seven weeks and weighing 175-200 g at reception, are placed two per cage and fed Purina rat chow for 1 week in order to acclimate them to the facility (sterile room with controlled temperature (22-24° C.) and alternating light and dark cycles). Food and water are provided ad libitum throughout the experiment. After achieving baseline cholesterol and triglyceride values over a three week period, the rats are randomly split into two groups, a control group (8 rats fed Purina rat chow) and a high cholesterol (HC) test group (16 rats fed Purina rat chow supplemented with 10% corn oil and 1.5% (wt/wt) cholesterol). Upon stabilization of the increased serum cholesterol levels in the test group, the cholesterol fed rats are randomly split into two equal groups for the purpose of running a control group of 8 rats fed a HC diet and empty microcapsules against a treatment group of 8 rats fed a HC diet and microcapsules containing LP80 (pCBH1). For the experiments, empty control microcapsules or microcapsules containing a suitable amount of log phase genetically engineered bacteria are suspended in 0.8-1.0 ml sterile normal saline in a 5 ml syringe. The floating microcapsules are orally forced fed to the test rats twice daily using curved 16G-3½ stainless steel gavage. Upon re-stabilization of the decreased serum cholesterol levels among the treatment group, the gavage feeding is stopped. Throughout the experiment, weight gain in each group is monitored weekly. Venous blood samples (500 uL) are collected every 4th day (preceded by a 12-14 hour fast) in serum clotting activator tubes. The samples are centrifuged at 2000 g for 20 minutes, and the supernatant serum is assayed for total cholesterol, HDL cholesterol and triglycerides using a Hitachi 911 clinical chemistry analyzer. LDL cholesterol is determined by formula. Fresh fecal samples are obtained on a weekly basis for analysis of excreted bile acids. Fecal bile acids are extracted by the method of van der Meer et al. (Usman & Hosono, 2000) and the supernatants are assayed enzymatically.

EXAMPLE 4

Experimental Hamster Model and In-Vivo Experimental Procedure

The second animal model employs male golden Syrian hamsters to evaluate the efficacy and safety of orally delivering microencapsulated live genetically engineered LP80 cells. The hamster is well-established for demonstrating cholesterol and bile acid metabolism that accurately mimics the human condition (Spady et al, 1985; Spady et al, 1986; Spady and Dietschy, 1988; Imray et al. 1992). In relation to animals of similar size, the hamster is unique in that it contains plasma cholesterol ester transfer protein and LDL-receptor mediated activities at levels similar to humans (Ahn et al, 1994; Chen et al, 1996; Remillard et al., 2001; Trautwein, E. A., 1993) and its closely suited lipoprotein profile is useful for studying the effects of diet and pharmaceutical products on lipoprotein metabolism (Bravo et al., 1994). Furthermore, the hamster requires only small increases in dietary cholesterol to induce elevations in plasma lipid and lipoprotein cholesterol concentrations (Terpstra et al. 1991; Kowala, 1993). In particular, the Bio $F_1B$ strain (BioBreeders USA) male golden Syrian hamster are employed because of its characteristic phenotype which promotes diet-induced hyperlipidemia and atherosclerotic lesion formation (Terpstra et al, 1991). When administered a diet of elevated cholesterol and saturated fat, the Bio $F_1B$ model shows increased serum cholesterol levels more significantly in the VLDL and LDL fraction, as compared to the HDL fraction, making the hyperlipidemic Bio $F_1B$ model more useful for mimicking the human situation than other strains (Trautwein et al., 1993; Kowala et al., 1991; Trautwein et al, 1993a).

For the in-vivo animal study, 24 male golden Syrian hamsters (strain Bio $F_1B$, BioBreeders USA), aged 4 weeks and weighing ~70 g at reception, are placed two per cage and fed rodent chow for 1 week in order to acclimate them to the facility (sterile room with controlled temperature (22-24° C.) and alternating light and dark cycles). Food and water are provided ad libitum. After baseline cholesterol and triglyceride values are noted over a period of three weeks, the hamsters are divided into two groups, a control group (8 hamsters fed rodent chow) and a test (HC) group (16 hamsters fed a nonpurified hypercholesterolemic diet consisting of rodent chow supplemented with 3% corn oil and 0.5% (wt/wt) cholesterol). Previous studies have shown that a nonpurified diet, as compared to a semipurified diet, induces a lipoprotein profile similar to humans (Wilson et al. 1999; Krause et al, 1992). Once the increasing serum cholesterol levels in the test group stabilize, the cholesterol fed hamsters are randomly split into two equal groups for the purpose of running a control group of 8 hamsters fed a HC diet and empty microcapsules, against a treatment group of 8 hamsters fed a HC diet and microcapsules containing LP80 (pCBH1) bacterial cells. For the experiments, empty control microcapsules or microcapsules containing a suitable amount of log phase genetically engineered bacteria are suspended in 0.8-1.0 ml sterile normal saline in a 5 ml syringe. The floating microcapsules are then orally forced fed to the test rats using curved 16G-3½ stainless steel gavage twice daily. Upon re-stabilization of the decreased serum cholesterol levels among the treatment group, the gavage feeding is stopped. Throughout the experiment, weight gain in each group is monitored weekly. Venous blood samples are collected every 4th day (preceded by a 12-14 hour fast) in serum clotting activator tubes. The samples are centrifuged, and the supernatant serum is assayed for total cholesterol, HDL cholesterol, and triglycerides using a Hitachi 911 clinical chemistry analyzer. LDL cholesterol is computed by formula. Fresh fecal samples are obtained on a weekly basis for analysis of excreted bile acids. Fecal bile acids are extracted by the method of van der Meer et al. (1985) and the supernatants are assayed enzymatically.

Results:
Baseline Period:

The results will show that the whole experimental group (EG) of animals will have an adequately homogeneous baseline level of blood serum cholesterol (TC, HDL and LDL), and triglycerides (TG). The results will also show that the EG will have homogeneous body weights, will eat and drink similar amounts, and gain weight within normal limits etc. Finally, the results will show that the free DCA concentration will be moderate in fecal samples of the EG group.

Cholesterol Feeding Period:

The results will show that the cholesterol fed group (HC) (⅔) of animals will have high TC, HDL, LDL, TG, and will gain weight while the animals remaining (⅓) in the EG will maintain their normal levels. The results will show that the HC group will eat slightly less food by weight but will eat a normal or slightly elevated number of calories, as they are eating food containing more calories. The results will show that the HC group will have an elevated level of free DCA in fecal samples while the remaining EG group will maintain normal levels.

Therapeutic Period:

The results will show that

1. The animals receiving micro LP80 (pCBH1) therapy in the HC group (½ the HC group) will achieve normalized levels of TC, HDL, LDL, and possibly TG to some extent;
2. while the empty micro group (placebo) will maintain previously high levels of TC, HDL, LDL, and TG;
3. and the outstanding EG will continue to show normal levels.

The results will show that free DCA levels may normalize in the treated group, but will be directly dependent on the microcapsule stability, survivability, and of course extraction techniques used (experimental conditions).

Normalization Period:

The results will show that when all animals are returned to the normal diet and the treatment with micro. is stopped that the remaining levels of the HC group, and in particular the placebo group, will normalize to the group of EG animals that have remained a control thorough.

EXAMPLE 5

Intraluminal Bile Acid Removal for Patients with Congenital Disease, Bowel Resection or Disease of the Bowel Patients need an effective and safe system for the removal of excess bile acids, because elevated intraluminal concentrations of deconjugated bile acids in the colon normally result in an increased secretion of electrolytes and water causing diarrhea (Hofmann, 1999). Microencapsulated LP80 (pCBHl) and/or *L. reuteri* and/or BSH enzyme is orally administered to deconjugate, precipitate, and then bind conjugated bile acids within the microcapsules thus avoiding problems associated with excessive electrolyte and water secretion and the resulting diarrhea.

EXAMPLE 6

Figure 9:
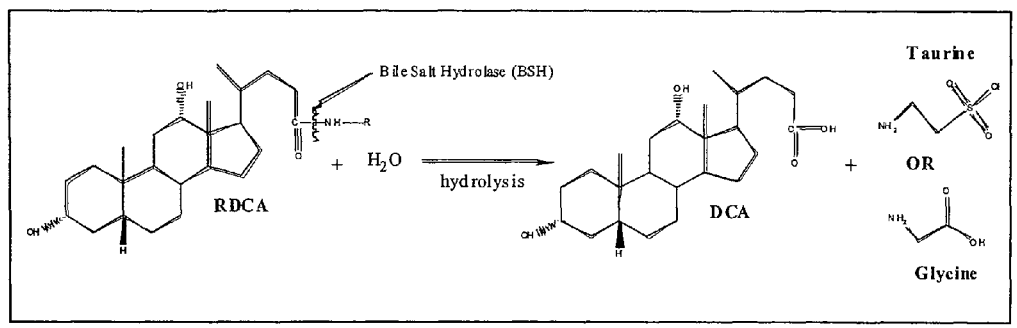
FIG. 9 illustrates hydrolysis of conjugated bile salts by the Bile Salt Hydrolase (BSH) enzyme overproduced by genetically engineered *Lactobacillus plantarum* 80 (pCBHl). R indicates the amino acid glycine or taurine. RDCA: glyco- or tauro-deoxycholic acid, DCA: deoxycholic acid.
Figure 10:
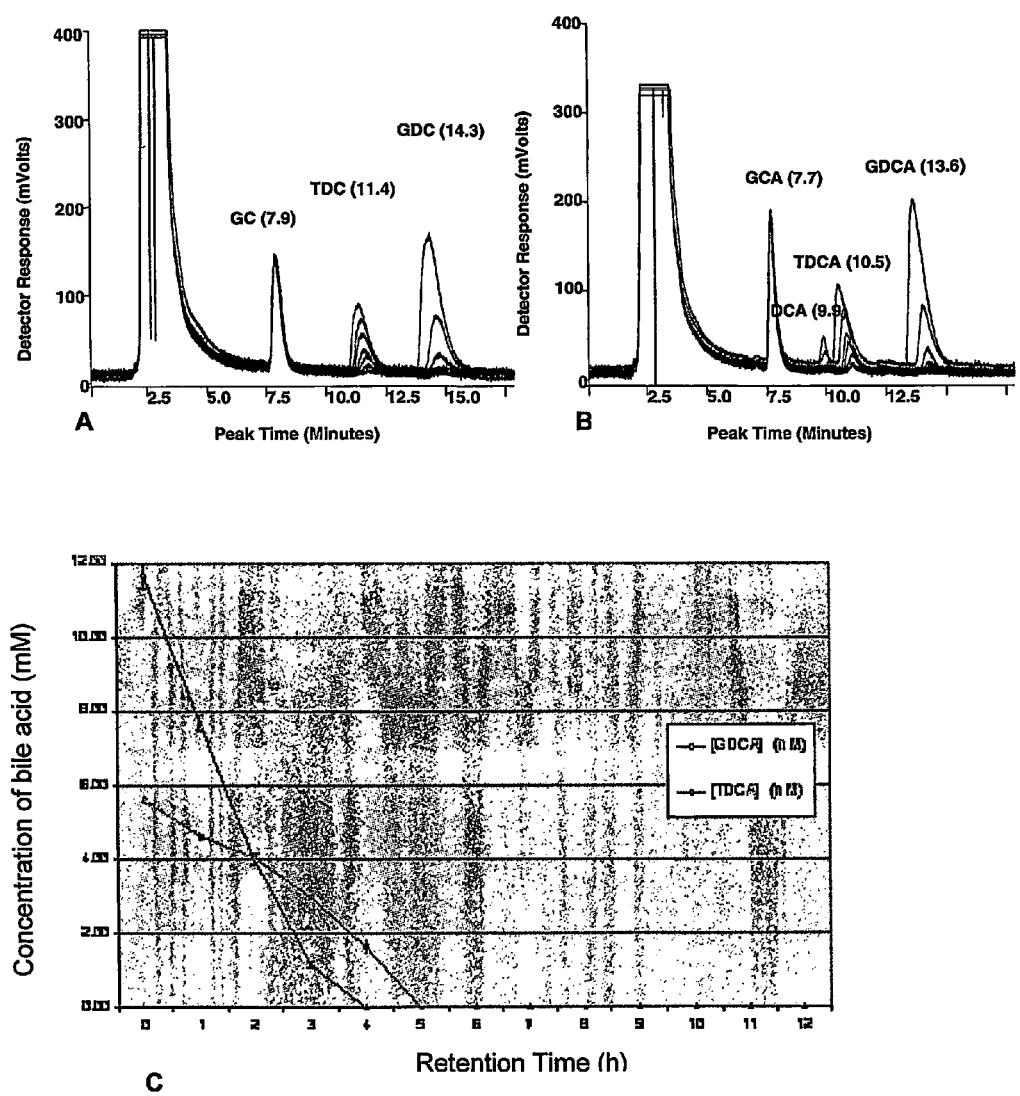
FIG. 10 illustrates (A) overlaid HPLC chromatograms of samples (0 h, 1 h, 2 h, 3 h, 4 h, 5 h, 6 h) from experiment in which microencapsulated LP80 (pCBH1) was used to deconjugate 10 mM GDCA and 5 mM TCDA. (B) Overlaid HPLC chromatograms of samples (0 h, 1 h, 2 h, 3 h, 4 h, 5 h, 6 h) from experiment in which immobilized LP80 (pCBH1) was used to deconjugate 10 mM GDCA and 5 mM TCDA. (C) Graphical representation (A), (D) Graphical representation of (B).
Figure 10:
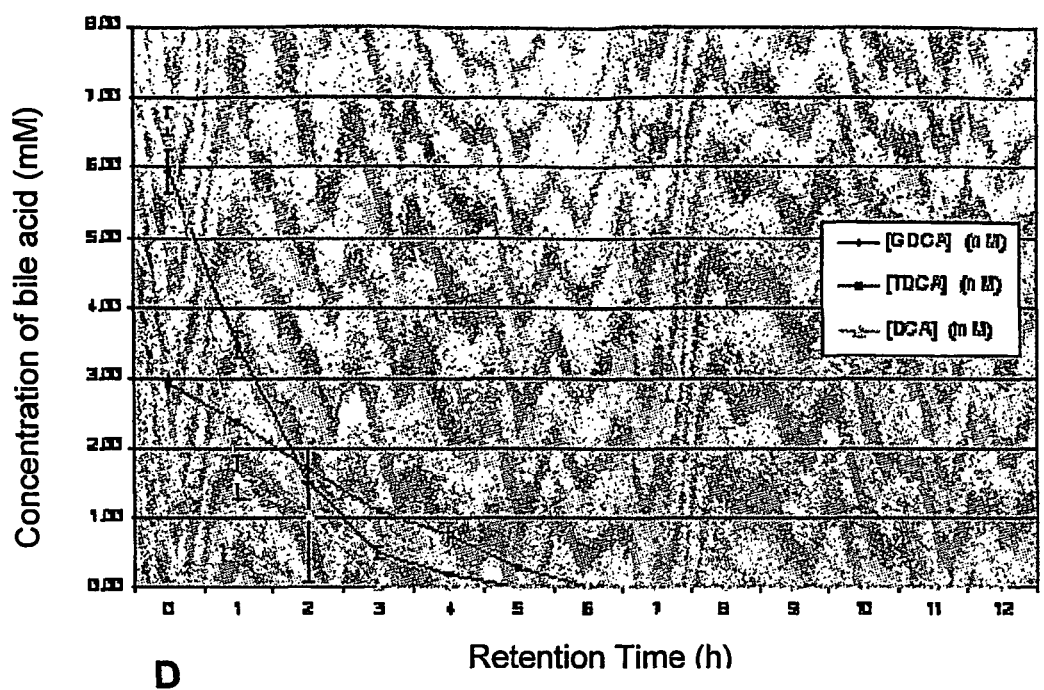

Bioavailability of Deoxycholic Acid (DCA) and Addressing the Potential Concerns of Bile Acid Deconjugation By-Products The BSH enzyme, overproduced by LP80 (pCBHl), releases glycine or taurine from the conjugated bile salt steroid core and generates deconjugated primary bile salts, which are less water-soluble and are excreted more easily via the faeces. This provides lowering of serum cholesterol with microencapsulated LP80 (pCBHl). As seen in FIGS. 10A and 10D, microencapsulated LP80 (pCBHl) was able to deconjugate GDCA and TDCA completely within 4 h and 5 h respectively. In other experiments, immobilized LP80 (pCBH1) was able to effectively break down GDCA and TDCA bile acids within 5 h and 6 h respectively (FIG. 10B). However, with immobilization the deconjugation product, deoxycholic acid (DCA), was detected (FIG. 10B, 10C). This shows that microencapsulated cells diminished the bioavailability of BSH deconjugated bile acids totally (FIG. 10) (FIG. 9). The proposed mechanism in explanation, without wishing to be bound by a particular explanation, is that with microencapsulation (as opposed to immobilization or free bacteria) there is decreased mass transfer of newly deconjugated DCA (by BSH from LP80 (pCBH1)) and that the added concentration and interaction time within the microcapsule allows for the total precipitation of DCA by calcium ions. The calcium may be produced by the immobilized bacteria or may be that which is bound within the alginate matrix originally from the CaCl polymerizing solution.

Figure 8:
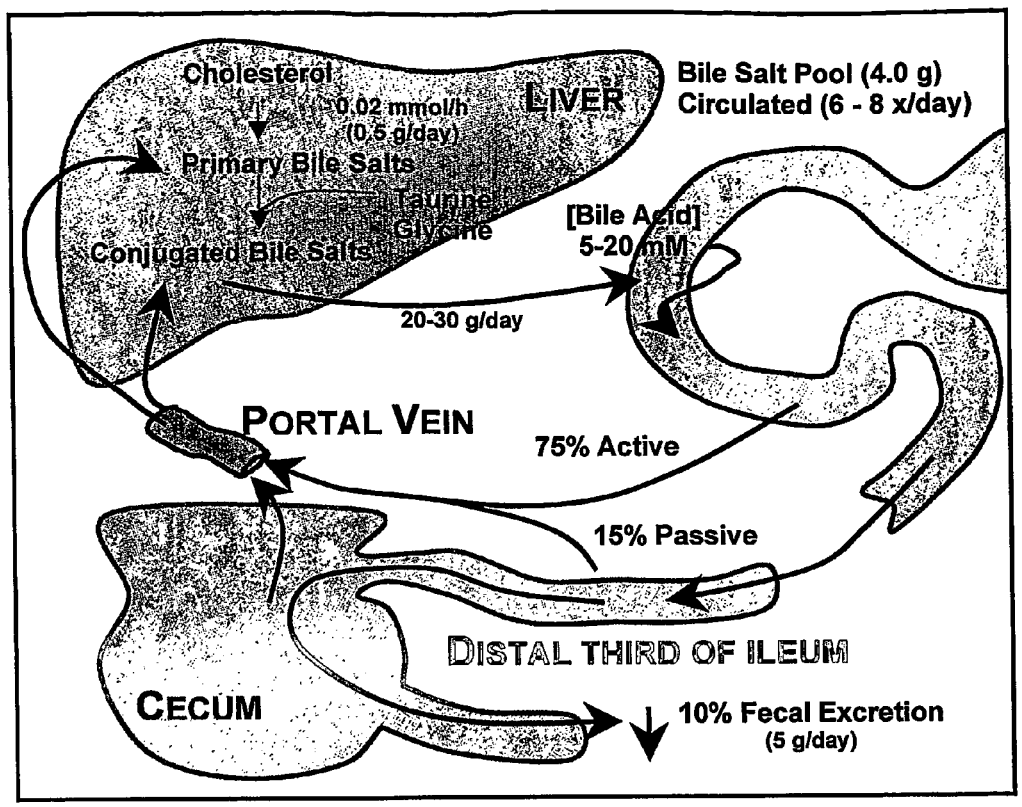
FIG. 8 illustrates the Enterohepatic circulation of bile (EHC)
Figure 11:
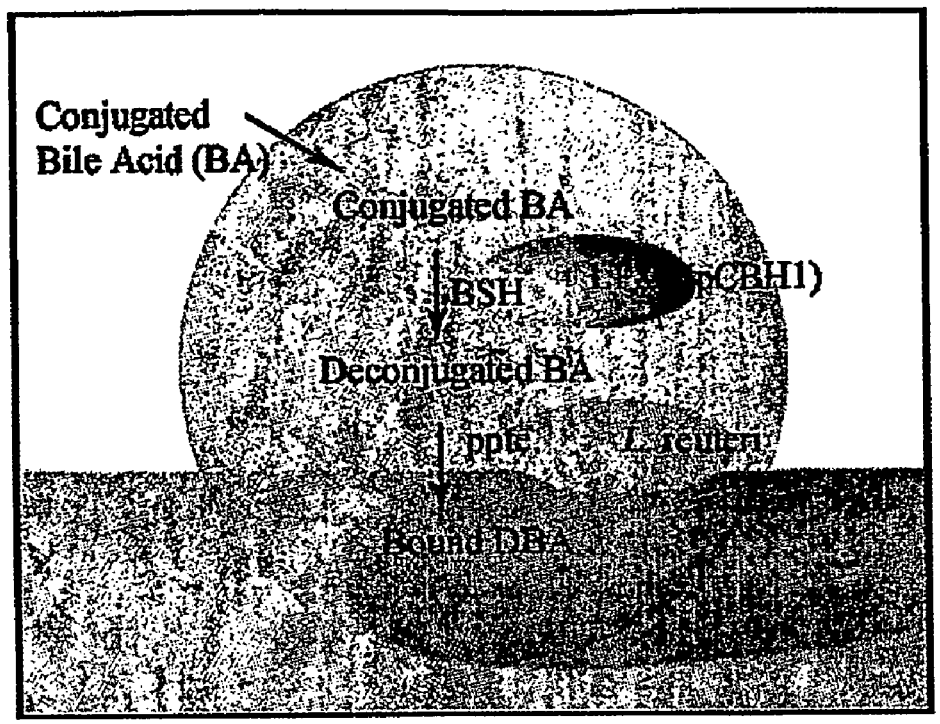
FIG. 11 illustrates APA microcapsules containing genetically engineered *Lactobacillus plantarum* 80 (pCBH1) and *L. reuteri*. BSH is overproduced by LP80 (pCBH1) cells and hydrolyzes available conjugated bile acids. *L. reuteri* precipitates and binds the produced deconjugated bile acids making them unable to leave the microcapsule and thus less bioavailable.

This finding improves the therapeutic properties of microencapsulated LP80 (pCBH1) in several ways. For example, it addresses concerns over the production of large amounts of deconjugated bile salts and their association with an increased risk of developing colon cancer. Also, if bile salts are actually being deconjugated, precipitated, and then bound within the microcapsule, microencapsulated LP80 (pCBH1) may be capable of removing all bile acid from the GI lumen. LP80 is only one example of a cell that overproduces BSH. The same result occurs with any cell that expresses BSH, any bacteria that expresses BSH, any cell extract containing BSH and with BSH enzyme itself. This effect contrasts previous results, using free bacteria, where the authors predicted only an improved clearance (from 95% for conjugated to 60% for deconjugated) of bile acids from the ECH and not total clearance (De Smet et al., 1994) (FIG. 8). Further, elevated intraluminal concentrations of deconjugated bile acids in the colon, normally resulting in an increased secretion of electrolytes and water and causing diarrhea (Hofmann, 1999), would cease to present difficulty, as the deconjugated bile acids would be entirely precipitated and bound within the microcapsules and excreted in the stool. Thus, the invention provides a method for reducing bile salts in an animal, comprising administering to the animal a capsule comprising an encapsulated agent for deconjugating and precipitating the bile salts to produce a bile salt derivative. The method further comprises binding the bile salt derivative to the capsule wherein the capsule and bile salt derivative are excreted by the animal Another method for dealing with the unwanted DCA byproduct is by co-encapsulating a bacterium specially intended for the purpose. Recent studies have shown that the adverse effects of deconjugated bile salts can be counteracted by the addition of another naturally occurring resident of the gastrointestinal tract, *L. reuteri* (De Smet et al., 1994). It appears that the cell toxicity, normally exhibited by deconjugated primary bile salts and the type produced by LP80 (pCBHl) BSH activity, is totally counteracted by the addition of *L. reuteri* (De Smet et al, 1994). *L. reuteri* precipitates the deconjugated bile salts and physically binds the bile salts making them less bioavailable. Thus, microencapsulated LP80 (pCBHl) holds yet another advantage over administration of the free bacteria. That is that *L. reuteri* bacteria is added to the LP80 (pCBHl) microcapsule so that the two bacteria work together, first deconjugating conjugated bile salts and then precipitating and binding deconjugated bile salts (FIG. 11). Thus, the invention provides a method for reducing bile salts in an animal, comprising administering to the animal a capsule comprising:

(a) a bacteria that deconjugates bile salts and
(b) a second bacteria that precipitates and binds the deconjugated bile salts.

In one embodiment, the first bacteria is *L. plantarum* and the second bacteria is *L. reuteri*.

This system may also work to improve the therapeutic properties of microencapsulated LP80 (pCBHl) in several ways. Firstly, by decreasing the deconjugated bile salts bioavailability it addresses the concerns that large amounts of deconjugated bile salts have been associated with an increased risk for colon cancer. Secondly, by deconjugating, precipitating and then binding the bile acids within the microcapsule, microencapsulated LP80 (pCBl) totality removes bile acid from the ECH, not just improving the possibility of bile acid excretion (from 95% for conjugated to 60% for deconjugated). This provides total control of the ECH in a noninvasive way (FIG. 8). Thirdly, elevated intraluminal concentrations of deconjugated bile acids in the colon which would normally result in an increased secretion of electrolytes and water causing diarrhea is no longer be a problem because the deconjugated bile acids are precipitated and bound within the microcapsules by *L. reuteri*. Finally, it is important to note that microencapsulating LP80 (pCBHl) and *L. reuteri* together allows for their protection from the low pH and harsh environment of the stomach contents, it gives them close proximity, and provides ideal conditions for this system of bile acid removal.

EXAMPLE 7

Combination Cholesterol Lowering Therapy

It is now well known that statins increase the risk of myopathy in patients receiving large dosages and in patients with renal or hepatic impairment, serious infections, hypothyroidism, or advanced age (Association, A.P. New Product Bulletin, 2002). In such patients, and in patients with an inadequate LDL lowering response to statins, it is widely accepted that combination therapy with a bile acid sequestrant or niacin should be considered (Association, A.P. New Product Bulletin, 2002; Brown et al, 2001; Gupta and Ito, 2002; Kashyap et al, 2002). Microencapsulated cells or bacteria such as LP80 (pCBH1) and/or *L. reuteri*, and/or free BSH enzyme are useful cholesterol lowering agents for use in combination therapy with statins and other lipid lowering therapies.

EXAMPLE 8

Preventative Therapy for Colon Cancer

Figure 12:
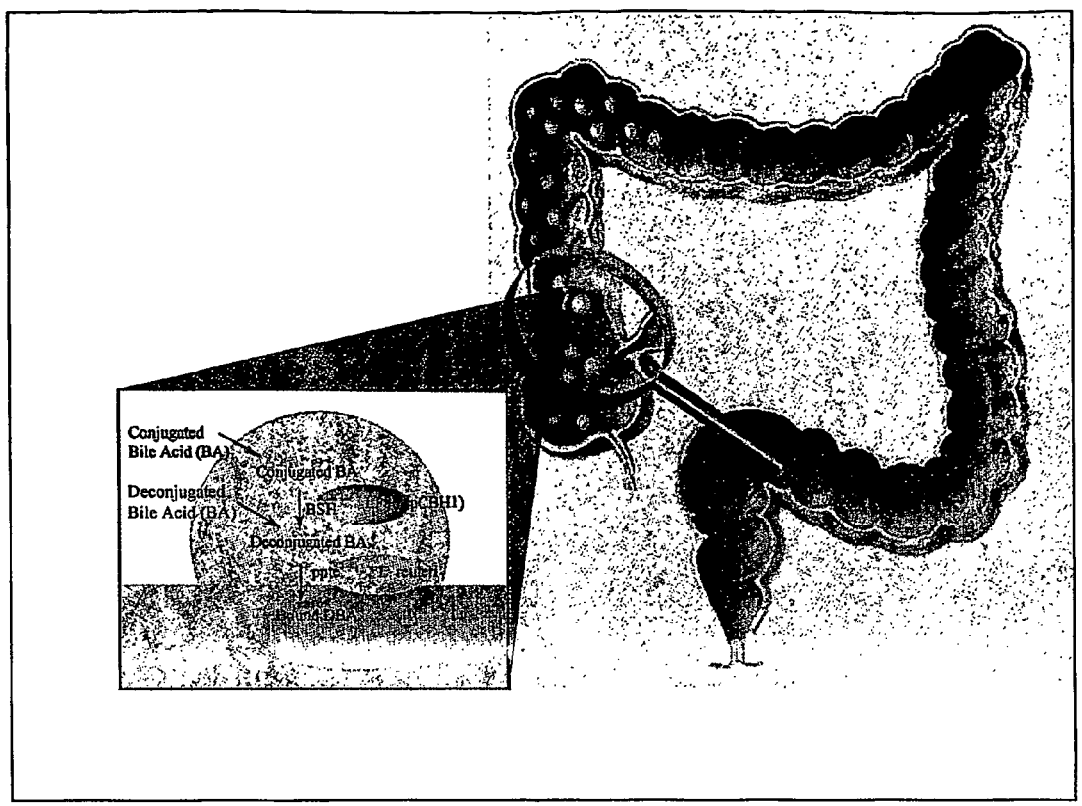
FIG. 12 illustrates APA microcapsules containing genetically engineered *Lactobacillus plantarum* 80 (pCBHl) and *L. reuteri*. BSH is overproduced by LP80 (pCBH1) cells and hydrolyzes available conjugated bile acids. *L. reuteri* precipitates and binds the produced deconjugated bile acids making them unable to leave the microcapsule and thus less bioavailable.

It is believed that thirty percent of all colon cancer deaths can be linked to diet (Stone and Papas, 1997). One mechanism for this close association is that a high fat diet leads to an increased secretion of primary bile salts into the small intestine, where the indigenous microflora deconjugates the primary bile acids. The increased biliary secretion leads to the formation of higher levels of deconjugated bile acids that may then exert their cytotoxic and mutagenic effect on the gastrointestinal. mucosa (Oumi and Yamamoto, 2000). It is these conjugated bile salts which have been incriminated in colonic carcinogenesis and thus a system for their removal would be a valuable tool for the prevention of colon cancer. Treatment with a composition of the invention, such as microencapsulated *L. reuteri* and/or microencapsulated LP80 (pCBHl) and *L. reuteri* together, removes unwanted and potentially harmful deconjugated bile acids, such as DCA, and provides a safe and effective means for patients and the public to prevent this deadly disease (FIG. 12).

EXAMPLE 9

In Vitro Diagnostic Tool for Liver Function and Hepatobiliary Diseases

Urinary levels of sulfated bile acids are known to be significantly elevated in liver disease and hepatobiliary disease (Back P., 1988). Several research groups have directed their efforts towards detection of these levels because urinary analysis is noninvasive, and urinary levels of sulfated bile acids are thought to be useful as an index of liver function and an indicator of hepatobiliary disease (Kobayashi et al, 2002).

Figure 13:
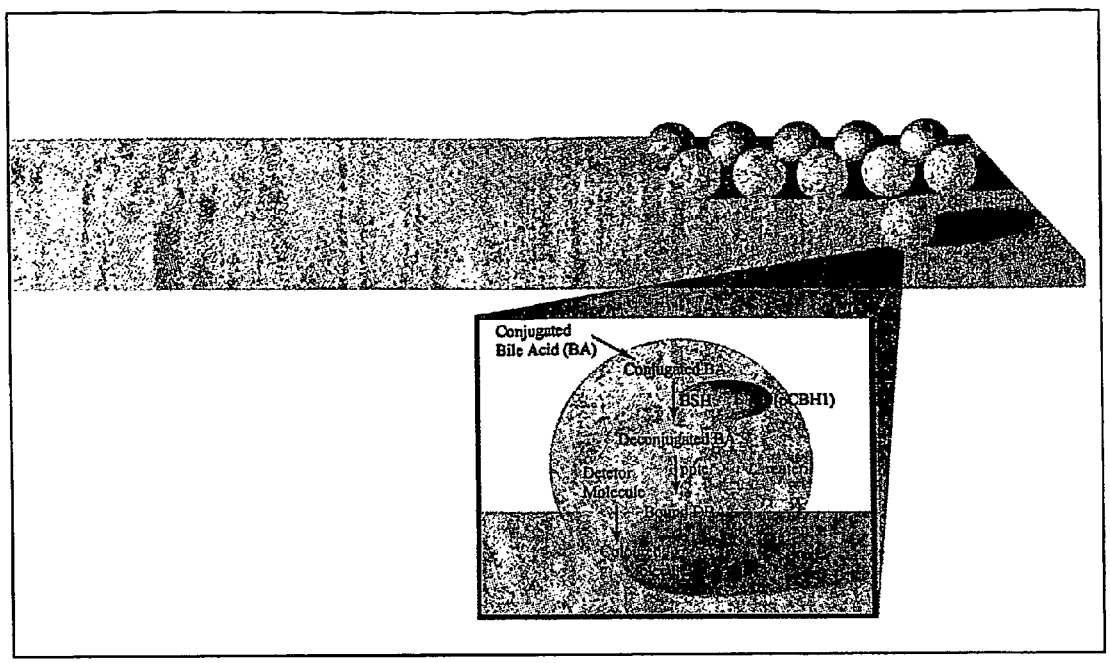
FIG. 13 illustrates diagnostic strip for determination of liver function and detection of hepatobilary diseases through detection of conjugated bile acids in urine. APA microcapsules containing genetically engineered LP80 (pCBHl) and *L. reuteri*, as well as a colored detector molecule for either the deconjugated bile acid or released amino acid, adhered to the functional end of a diagnostic strip. BSH is overproduced by LP80 (pCBHl) cells and hydrolyzes available conjugated bile acids. *L. reuteri* precipitates and binds the produced deconjugated bile acids. A colored detector molecule would react with either the deconjugated bile acid or released amino acid groups and produce a discernable change in color. (BA) is bile acid. (DBA) is deconjugated bile acid.

A diagnostic strip containing immobilized beads and/or microcapsules containing cells expressing BSH such as LP80 (pCBHl) and/or *L. reuteri*, and/or the BSH enzyme itself as well as a colored detector molecule, is used as a novel noninvasive diagnostic tool for liver function and hepatobiliary diseases in urine (FIG. 13). BSH is overproduced by LP80 (pCBHl) cells and hydrolyzes available conjugated bile acids. *L. reuteri* precipitates and binds the produced deconjugated bile acids. The colored detector molecule reacts with either the deconjugated bile acid or the released amino acid groups from deconjugation and produces a perceptible change in color. This diagnostic strip may be readily adapted for use with lipase to diagnose elevated triglyceride levels.

EXAMPLE 10

Component of Integrated Bioartificial Liver

Figure 14:
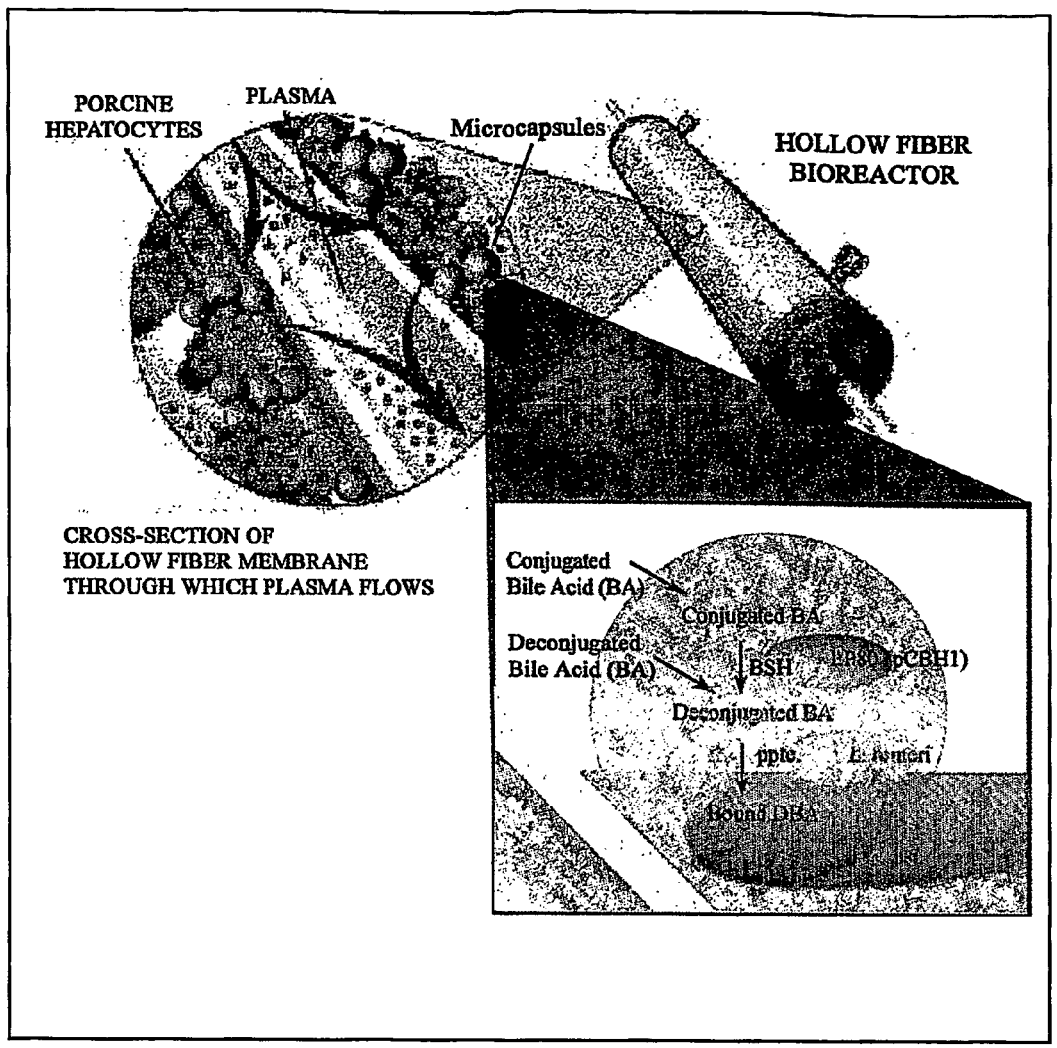
FIG. 14 illustrates the hollow fiber membrane of a bioartificial liver (BAL) is impregnated with hepatocytes and APA microcapsules containing genetically engineered *Lactobacillus plantarum* 80 (pCBHl) and *L. reuteri*. BSH is overproduced by LP80 (pCBHl) cells and hydrolyzes available conjugated bile acids. *L. reuteri* precipitates and binds the produced deconjugated bile acids making them unable to leave the microcapsule.

Incorporation of immobilized beads and/or microcapsules containing cells expressing BSH, such as *Lactobacillus plantarum* 80 (pCBHl) (LP80 (pCBH1)) and/or *Lactobacillus reuteri* (*L. reuteri*) and/or BSH enzyme is useful if incorporated into a bioartificial liver for the removal of unwanted bile acids that build up during liver disease. It is well known that the bioartificial liver (BAL) must provide both synthetic and detoxifying functions (Rozga et al, 1993; Schafer and Shaw, 1989) normally performed by the liver. Several groups have developed a BAL consisting of isolated porcine (Abouna et al., 1999; Morsiani et al., 1998) or bovine hepatocytes in a hollow-fiber bioreactor. Recently, researchers have focused on the use of BAL to support patients with fulminant hepatic failure (FHF), in which impaired liver function is associated with pathologically elevated levels of bile acids. In this case an effective BAL requires the ability to remove and process a significant quantity of deconjugated bile acid. Incorporation of immobilized beads and/or microcapsules containing LP80 (pCBHl) and/or *L. reuteri* is used for the removal of unwanted and pathologically high levels of bile acids if incorporated into a bioartificial liver (FIG. 14).

EXAMPLE 11

Lipase Degradation of Triglyceride

Purified Lipase enzyme is microencapsulated/immobilized (Lipase, type VII, from *Candidida rugosa*, containing lactose as an extender, from Sigma) in APA or other membrane using procedures as indicated above. Microencapsulation of any lipase is useful. A simple batch bioreactor (one-step in-vitro method) is used to incubate the microLipase with various concentrations of triglycerides (TG) at duodenal pH (7-4) for the approximately 4 hour transit time and samples are removed at regular intervals for TG measurement. This procedure is optionally repeated in a Simulated Human Gastrointestinal Model (SHIME) whereby the low pH (1-2) environment of the stomach, correct transit times, neutralization, and the normal human pancreatic enzymes are simulated. The samples are also optionally tested in spectrophotometer-type assay, for example, on a Hitachi 911 clinical chemistry analyzer.

Reaction:

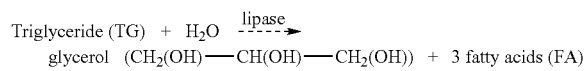

The addition of microLipase to the reaction flask provides an immediate decrease in the triglyceride concentration and causes the release of glycerol and free fatty acids. The results of this experiment show that encapsulated lipase is useful for treating the condition (disorder) Steatorrhea which is most often associated with disease of the pancreas and small bowel.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

All publications, patents and patent applications, including the priority application U.S. patent application No. 60/450,334 filed Feb. 28, 2003, are herein incorporated by reference in their entirety to the same extent as if each individual publication, patent or patent application was specifically and individually indicated to be incorporated by reference in its entirety.

REFERENCES

Abouna, G. M., Ganguly, P. K., Hamdy, H. M., Jabur, S. S., Tweed, W. A., & Costa, G. Extracorporeal liver perfusion system for successful hepatic support pending liver regeneration or liver transplantation: a pre-clinical controlled trial. *Transplantation* 67, 1576-1583 (1999).

Ahn, Y. S., Smith, D., Osada, J., Li, Z., Schaefer, E. J., & Ordovas, J. M. Dietary fat saturation affects apolipoprotein gene expression and high density lipoprotein size distribution in golden Syrian hamsters. *J Nutr* 124, 2147-2155 (1994).

Ambrosino, G., Varatto, S., & Basso S. Hepatocyte transplantation in the Treatment of acute liver failure: microencapsulated hepatocytes vs. hepatocytes attached to an autologous biomatrix. Cell transplantation. vol. 12 p. 4349) (2003)

Anderson, J. W. & Gilliland, S. E. Effect of fermented milk (yogurt) containing *Lactobacillus acidophilus* L1 on serum cholesterol in hypercholesterolemic humans. *J. Am. Coll. Nutr.* 18, 43-50 (1999).

Association, A.P. New Product Bulletin: Advicor (niacin extended-release and lovostatin). 2002.
Ref Type: Report Attanasio, E., Russo, P., & Allen, S. E. Cost-minimization analysis of simvastatin versus atorvastatin for maintenance therapy in patients with coronary or peripheral vascular disease. *Clin Ther.* 23, 276-283 (2001).

Back P. in The bile acids: chemistry, physiology, and metabolism. vol 4. Methods and applications, Vol. 4. eds. Setchell K D R, Kritchevski D, & Nair P P 405-440 (Plenum Press, New York; 1988).

Bravo, E., Cantafora, A., Calcabrini, A., & Ortu, G. Why prefer the golden Syrian-Hamster (Mesocricetus-Auratus) to the Wistar Rat in experimental studies on plasma-lipoprotein metabolism. *Comp. Biochem, Physiol.* 107, 347-355 (1994).

Brown, B. G., Zhao, X. Q., Chait, A., Fisher, L. D., Cheung, M. C., Morse, J. S., Dowdy, A. A., Marino, E. K., Bolson, E. L., Alaupovic; P., Frohlich, J., & Albers, J. J. Simvastatin and niacin, antioxidant vitamins, or the combination for the prevention of coronary disease. *N. Engl. J. Med.* 345, 1583-1592 (2001).

Cantafora, A., Di Biase, A., Alvaro, D., & Angelico, M. Improved method for measuring the glycine and taurine conjugates of bile salts by high-performance liquid chromatography with tauro-7 alpha,12 alpha-dihydroxy-5 beta-cholanic acid as internal standard. *J. Chromatogr.* 386, 367-370 (1987).

Chang, P. L. Encapsulation for somatic gene therapy. *Ann. N.Y. Acad. Sci.* 875, 146-158 (1999).

Chang, T. M. S. Semipermeable microcapsules. *Science* 146, 524-525 (1964).

Chang, T. M. & Prakash, S. Artificial cells for bioencapsulation of cells and genetically engineered *E. coli*. For cell therapy, gene therapy, and removal of urea and ammonia *Methods Mol. Biol.* 63, 343-358 (1997).

Chang, T. M. & Prakash, S. Therapeutic uses of microencapsulated genetically engineered cells. *Mol. Med Today* 4, 221-227 (1998).

Chang T M, & Prakash S. Procedures for microencapsulation of enzymes, cells and genetically engineered microorganisms. Mol. Biotechnol. 17(3): 249-260 (2001)

Chen, J., Song, W., & Redinger, R. Effects of dietary cholesterol on hepatic production of lipids and lipoproteins in isolated hamster liver. *J. Nutr* 124, 2147-2155 (1996).

Chin, J., Turner, B., Barchia, I., & Mullbacher, A. Immune response to orally consumed antigens and probiotic bacteria *Immunol. Cell Biol.* 78, 55-66 (2000).

Christiaens, H., Leer, R. J., Pouwels, P. H., & Verstraete, W. Cloning and expression of a conjugated bile acid hydrolase gene from *Lactobacillus plantarum* by using a direct plate assay. *Appl. Environ. Microbiol.* 58, 3792-3798 (1992).

Coca, E., Ribas, B., & Trigueros, G. A method for quick determination of bile acids in bile of patients with biliary lithiasis. *J. of Liquid Chromatogr.* 17, 1349-1363 (1994).

De Boever, P. & Verstraete, W. Bile salt deconjugation by *lactobacillus plantarum* 80 and its implication for bacterial toxicity. *J. Appl. Microbiol.* 87, 345-352 (1999).

De Boever, P., Wouters, R., Verschaeve, L., Berckmans, P., Schoeters, G., & Verstraete, W. Protective effect of the bile salt hydrolase-active *Lactobacillus reuteri* against bile salt cytotoxicity. *Appl. Microbiol. Biotechnol.* 53, 709-714 (2000).

De, Smet., I, De Boever, P., & Verstraete, W. Cholesterol lowering in pigs through enhanced bacterial bile salt hydrolase activity. *Br. J. Nutr.* 79, 185-194 (1998).

De, Smet., I, Van Hoorde, L., De Saeyer, M., Vande, W. M., & Verstraete, W. In vitro study of bile salt hydrolase (bsh) activity of bsh isogenic *lactobacillus plantarum* 80 strains an destination of cholesterol lowering through enhanced bsh activity. *Microbial ecology in health and disease* 7, 315-329 (1994).

Dunn-Emke, S., Weidner, G., & Ornish, D. Benefits of a low-fat plant-based diet. *Obes. Res.* 9, 731 (2001).

Gupta, E. K. & Ito, M. K. Lovastatin and extended-release niacin combination product: the first drug combination for the management of hyperlipidemia. *Heart Dis.* 4, 124-137 (2002).

Hodgson, T. A. & Cohen, A. J. Medical care expenditures for selected circulatory diseases: opportunities for reducing national health expenditures. *Med. Care* 37, 994-1012 (1999).

Hofmann, A. F. Bile Acids: The Good, the Bad, and the Ugly. *News Physiol Sci.* 14, 24-29 (1999).

Imray, C. H., Minoura, T., Davis, A., Radley, S., Newbold, K. M., Lavelle-Jones, M., Lawson, A. M., Baker, P. R., & Neoptolemos, J. P. Comparability of hamster with human faecal unconjugated bile acids in a model of colorectal cancer. *Anticancer Res.* 12, 553-558 (1992).

Jones, M. L., Hongmei, C., Ouyang, W., Metz, T., & Prakash, S. Method for Bile Acid Determination by High Performance Liquid Chromatography. *Journal of Medical Sciences* 23, 277-280 (2003).

Kashyap, M. L., McGovern, M. E., Berra, K., Guyton, J. R., Kwiterovich, P. O., Harper, W. L., Toth, P. D., Favrot, L. K., Kerzner, B., Nash, S. D., Bays, H. E., & Simmons, P. D. Long-term safety and efficacy of a once-daily niacin/lovastatin formulation for patients with dyslipidemia. *Am. J. Cardiol* 89, 672-678 (2002).

Kobayashi, N., Katsumata, H., Uto, Y., Goto, J., Niwa, T., Kobayashi, K., & Mizuuchi, Y. A monoclonal antibody-based enzyme-linked immunosorbent assay of glycolithocholic acid sulfate in human urine for liver function test. *Steroids* 67, 827-833 (2002).

Kowala, M. Effects of an atherogenic diet on lipoprotein cholesterol profile in the F1B hybrid hamster. *Atherosclerosis* 103, 293-294 (1993).

Kowala, M., Nunnari, J., Durham, S., & Nicolosi, R. Doxazosin and cholestyramine similarly decrease fatty streak formation in the aortic arch of hyperlipidemic hamsters. *Atherosclerosis* 91, 35-49 (1991).

Krause, B., Bousley, R., Kieft, K., & Stanfield, R. Effect of the ACAT inhibitor CI-976 on plasma cholesterol concentrations and distribution in hamsters fed zero- and no-cholesterol diets. *Clin Biochem* 25, 371-377 (1992).

Lichtenstein, A. H. Effects of diet and exercise on cholesterol levels. *N. Engl. J. Med.* 339, 1552-1553 (1998).

Lim, F. & Sun, A. M. Microencapsulated islets as bioartificial endocrine pancreas. *Science* 210, 908-910 (1980).

Moraga, F., Lindgren, S., & Janciauskiene, S. Effects of Non-inhibitory AAT on Primary Human Monocytes Activation in Vitro. Archives of Biochemistry and Biophysics. Vol. 386. p. 221-26 (2001).

Morsiani, E., Pazzi, P., Moscioni, A. D., Rozga, J., Azzena, G., & Demetriou, A. A. In vitro morphological and functional characterization of isolated porcine hepatocytes for extracorporeal liver support: bile acid uptake and conjugation. *J. Surg. Res.* 79, 54-60 (1998).

Muraji, T., Harada, T., Miki, K., Moriuchi, T., Obatake, M., Tsugawa. C. Urinary sulfated bile acid concentrations in infants with biliary atresia and breast-feeding jaundice. *Pediatrics International* 45(3), 281 (2003)

Ornish, D. & Denke, M. Dietary treatment of hyperlipidemia. *J. Cardiovasc. Risk* 1, 283-286 (1994).

Ornish, D., Scherwitz, L. W., Billings, J. H., Brown, S. E., Gould, K. L., Merritt, T. A., Sparler, S., Armstrong, W. T., Ports, T. A., Kirkeeide, R. L., Hogeboom, C., & Brand, R. J. Intensive lifestyle changes for reversal of coronary heart disease. *JAMA* 280, 2001-2007 (1998).

Oumi, M. & Yamamoto, T. A scanning electron microscope study on the effects of different bile salts on the epithelial lining of jejunal mucosa. *Med. Electron Microsc.* 33, 11-15 (2000).

Prakash, S. & Chang, T. M. In vitro and in vivo uric acid lowering by artificial cells containing microencapsulated genetically engineered *E. coli* DH5 cells. *Int. J Artif Organs* 23, 429-435 (2000).

Prakash, S. & Chang, T. M. Microencapsulated genetically engineered live *E. coli* DH5 cells administered orally to maintain normal plasma urea level in uremic rats. *Nat. Med* 2, 883-887 (1996).

Prakash, S. & Chang, T. M. Microencapsulated genetically engineered *E. coli* DH5 cells for plasma urea and ammonia removal based on: 1. Column bioreactor and 2. Oral administration in uremic rats. *Artif. Cells Blood Substit. Immobil. Biotechnol.* 24, 201-218 (1996a).

Prakash, S. & Chang, T. M. Growth kinetics of genetically engineered *E. coli* DH 5 cells in artificial cell APA membrane microcapsules: preliminary report. *Artif. Cells Blood Substit. Immobil. Biotechnol.* 27, 291-301 (1999).

Prakash, S. & Chang, T. M. Artificial cell microcapsules containing genetically engineered *E. coli* DH5 cells for in-vitro lowering of plasma potassium, phosphate, magnesium, sodium, chloride, uric acid, cholesterol, and creatinine: a preliminary report. *Artif. Cells Blood Substit. Immobil. Biotechnol.* 27, 475-481 (1999a).

Prakash, S. and Jones M. L. Engineering Artificial Cells for Therapy. Jul. 22, 2002. Sarawak, Malaysia, 2nd World Engineering Congress.
Ref Type: Conference Proceeding Prosser, L. A., Stinnett, A. A., Goldman, P. A., Williams, L. W., Hunink, M. G., Goldman, L., & Weinstein, M. C. Cost-effectiveness of cholesterol-lowering therapies according to selected patient characteristics. *Ann. Intern. Med* 132, 769-779 (2000).

Reckless, J. P. Economic issues in coronary heart disease prevention. *Curr. Opin. Lipidol.* 7, 356-362 (1996).

Remillard, P., Shen, G., Milne, R., & Maheux, P. Induction of cholesteryl ester transfer protein in adipose tissue and plasma of the fructose-fed hamster. *Life Sci* 69, 677-687 (2001).

Rozga, J., Williams, F., Ro, M. S., Neuzil, D. F., Giorgio, T. D., Backfisch, G., Moscioni, A. D., Hakim, R, & Demetriou, A. A. Development of a bioartificial liver: properties and function of a hollow-fiber module inoculated with liver cells. *Hepatology* 17, 258-265 (1993).

Scalia, S. Simultaneous determination of free and conjugated bile acids in human gastric juice by high-performance liquid chromatography. *J. Chromatogr.* 431, 259-269 (1988).

Schafer, D. F. & Shaw, B. W., Jr. Fulminant hepatic failure and orthotopic liver transplantation. *Semin Liver Dis.* 9, 189-194 (1989).

Sefton, M. V., May, M. H., Lahooti, S., & Babensee, J. E. Making microencapsulation work: conformal coating, immobilization gels and in vivo performance. *J. Control Release* 65, 173-186 (2000).

Spady, D. K. & Dietschy, J. M. Interaction of dietary cholesterol and triglycerides in the regulation of hepatic low density lipoprotein transport in the hamster. *J. Clin Invest* 81, 300-309 (1988).

Spady, D. K., Stange, E. F. B. L. E., & Dietschy, J. M. Bile acids regulate hepatic low density lipoprotein receptor activity in the hamster by altering cholesterol flux across the liver. *Proc. Natl. Acad Sci.* 83, 1916-1920 (1986).

Spady, D. K., Turley, S. D., & Dietschy, J. M. Rates of low density lipoprotein uptake and cholesterol synthesis are regulated independently in the liver. *J. Lipid Res.* 26, 465-472 (1985).

Stone, W. L. & Papas, A. M. Tocopherols and the etiology of colon cancer. *J. Natl. Cancer Inst.* 89, 1006-1014 (1997).

Taranto, M. P., Medici, M., Perdigon, G., Ruiz Holgado, A. P., & Valdez, G. F. Effect of *Lactobacillus reuteri* on the prevention of hypercholesterolemia in mice. *J. Dairy Sci.* 83, 401-403 (2000).

Terpstra, A., Holmes, J., & Nicolosi, R. The hypocholesterolemic effect of dietary soybean protein vs casein in hamsters fed cholesterol-free or cholesterol-enriched semipurified diets. *J. Nutr* 121, 944-947 (1991).

Trautwein, E. A., Liang, J., & Hayes, K. C. Cholesterol gallstone induction in hamsters reflects strain differences in plasma lipoproteins and bile acid profiles. *Lipids* 28, 305-312 (1993).

Trautwein, E. A., Liang, J., & Hayes, K. C. Plasma lipoproteins, biliary lipids and bile acid profile differ in various strains of Syrian hamsters, mesocritus auratus. *Comp. Biochem, Physiol.* 104, 829-835 (1993a).

Uludag, H., De Vos, P., & Tresco, P. A. Technology of mammalian cell encapsulation. *Adv. Drug Deliv.* Rev. 42, 29-64 (2000).

Usman & Hosono, A. Effect of administration of *Lactobacillus gasseri* on serum lipids and fecal steroids in hypercholesterolemic rats. *J. Dairy Sci.* 83, 1705-1711 (2000).

Van der Meer, R., De Vries, H., & Glatz, J. t-Butanol extraction of feces: a rapid procedure for enzymatic determination of fecal bile acids. *Cholesterol Metabolism in Health and Disease* 113-137 (1985).

Wilson, T., Nicolosi, R., Lawton, C., & Babiak, J. Gender differences in response to a hypercholesterolemic diet in hamsters: effects on plasma lipoprotein cholesterol concentrations and early aortic atherosclerosis. *Atherosclerosis* 146, 83-91 (1999).

What is claimed is:

1. A composition comprising:
   a. a bile-permeable microcapsule comprising a cell expressing a bile acid deconjugating enzyme in an amount sufficient to deconjugate bile in the microcapsule in the small intestine; and
   b. a carrier;
   wherein the bile-permeable microcapsule permits entry of bile and retains at least a portion of bile acid precipitate produced from the bile by the bile acid deconjugating enzyme.

2. The composition of claim 1, wherein the bile acid deconjugating enzyme is present in an amount sufficient to lower serum cholesterol.

3. The composition of claim 1, wherein the microcapsule reduces exposure of the cell to antibodies compared to a nonencapsulated cell, but permits exposure to nutrients.

4. The composition of claim 1, wherein the microcapsule comprises a polymer bead and the cell is immobilized in the bead.

5. The composition of claim 1, wherein the enzyme deconjugates bile acid to the bile acid precipitate.

6. The composition of claim 5, wherein the bile acid precipitate comprises deoxycholic acid (DCA) precipitate or a cholic acid precipitate.

7. The composition of claim 1, wherein the cell is a bacterial cell.

8. The composition of claim 7, wherein the bacterial cell is an anaerobic bacterial cell.

9. The composition of claim 7, wherein the cell is genetically engineered.

10. The composition of claim 7, wherein the bacterial cell is *Lactobacillus*.

11. The composition of claim 7, wherein the bacterial cell is *Lactobacillus plantarum, Lactobacillus reuteri, Bifidobacterium bifidum, Lactobacillus acidophilus* or *Clostridium perfringens*.

12. The composition of claim 11, wherein the bacteria cell is *Lactobacillus reuteri*.

13. The composition of claim 1, wherein the bile acid deconjugating enzyme is bile salt hydrolase (BSH).

14. The composition of claim 13, wherein the BSH is encoded by a nucleotide sequence as shown in SEQ ID NO: 1.

15. The composition of claim 1, wherein the microcapsule comprises a synthetic polymer.

16. The composition of claim 15, wherein the synthetic polymer comprises polylactide, polyglycolic acid or polyanhydride.

17. The composition of claim 1, wherein the microcapsule comprises alginate-polylysine-alginate (APA).

18. The composition of claim 1, wherein the microcapsule comprises Alginate/Poly-l-lysine/Pectin/Poly-l-lysine/Alginate (APPPA), Alginate/Poly-l-lysine/Pectin/Poly-l-lysine/Pectin (APPPP), Alginate/Poly-L-lysine/Chitosan/Poly-l-lysine/Alginate (APCPA), or alginate-polymethylene-co-guanidine-alginate (A-PMCG-A).

19. The composition of claim 1, wherein the microcapsule comprises Alginate/Poly-l-lysine/Pectin/Poly-l-lysine/Alginate (APPPA), Alginate/Poly-l-lysine/Pectin/Poly-l-lysine/Pectin (APPPP), Alginate/Poly-L-lysine/Chitosan/Poly-l-lysine/Alginate (APCPA), alginate-polymethylene-co-guanidine-alginate (A-PMCG-A), hydroxymethylacrylate-methyl methacrylate (HEMA-MMA), Multilayered HEMA-MMA-MAA, polyacrylonitrilevinylchloride (PAN-PVC), acrylonitirle/sodium methallylsuflonate (AN-69), polyethylene glycol/poly pentamethylcyclopentasiloxane/polydimethylsiloxane (PEG/PD$_5$/PDMS) or poly N,N-dimethyl acrylamide (PDMAAm) membranes.

20. The composition of claim 1, wherein the microcapsule comprises polyamide, lipid-complexed polymer, a lipid vesicle, a siliceous encapsulate, calcium alginate, k-carrageenan-Locust bean gum gel beads, gellan-xanthan beads, poly(lactide-co-glycolides), carageenan, starch polyanhydrides, starch polymethacrylates, polyamino acids or enteric coating polymers.

21. The composition of claim 1, wherein the bile-permeable microcapsule has a molecular weight cutoff point (MWCO) of 3000 D to 950,000 D.

22. The composition of claim 1, wherein the carrier comprises an orally administrable carrier.

23. The composition of claim 1, wherein the carrier comprises a nutraceutical or functional food product.

24. The composition of claim 1, wherein the carrier is implantable.

25. The composition of claim 1, wherein the composition is a pharmaceutical composition and the carrier is a pharmaceutically acceptable carrier.

26. The composition of claim 1, further comprising an additional cholesterol lowering therapeutic.

27. The composition of claim 26, wherein the additional cholesterol lowering therapeutic is selected from the group consisting of bile acid sequesterant (BAS) Cholestyramine resin, Colesevelam, Colestipol, statin, a probiotic formulation containing other live bacterial cells and neutraceuticals, and natural cholesterol lowering products.

28. The composition of claim 27, wherein the statin is selected from the group consisting of lovastatin, pravastatin, simvastatin, fluvastatin, and atorvastatin.

29. The composition of claim 1, wherein the microcapsule is resistant to degradation by bile.

30. The composition of claim 1, wherein the bile-permeable microcapsule has a molecular weight cutoff point (MWCO) of 5000 D to 750,000 D.

31. The composition of claim 1, wherein the bile-permeable microcapsule has a molecular weight cutoff point (MWCO) of 10000 D to 500,000 D.

32. The composition of claim 7, wherein the bacterial cell is *Bifidobacteria*.

\* \* \* \* \*